United States Patent [19]
Chio

[11] Patent Number: 6,165,130
[45] Date of Patent: Dec. 26, 2000

[54] METHOD FOR DIAGNOSING, MONITORING AND TREATING HYPERTENSION AND OTHER CARDIAC PROBLEMS

[75] Inventor: Shiu-Shin Chio, San Diego, Calif.

[73] Assignee: Pulse Metric, Inc., San Diego, Calif.

[21] Appl. No.: 09/191,337

[22] Filed: Nov. 13, 1998

Related U.S. Application Data

[62] Division of application No. 08/169,590, Dec. 17, 1993, Pat. No. 5,836,884.

[51] Int. Cl.$^7$ ........................................................... A61B 5/02
[52] U.S. Cl. ............................................ 600/485; 600/526
[58] Field of Search ..................................... 600/481, 485, 600/500, 501, 504, 506, 507, 526

[56] References Cited

U.S. PATENT DOCUMENTS

| | | |
|---|---|---|
| 4,562,843 | 1/1986 | Djordjevich et al. . |
| 4,834,107 | 5/1989 | Warner . |
| 4,880,013 | 11/1989 | Chio . |
| 5,054,493 | 10/1991 | Cohn et al. . |
| 5,162,991 | 11/1992 | Chio . |
| 5,211,177 | 5/1993 | Chesney et al. . |
| 5,265,615 | 11/1993 | Frank et al. . |
| 5,370,122 | 12/1994 | Kunig et al. . |
| 5,400,793 | 3/1995 | Wesseling . |

FOREIGN PATENT DOCUMENTS

| | | |
|---|---|---|
| 1031185 | 5/1978 | Canada . |
| 2 318 612 | 2/1977 | France . |

OTHER PUBLICATIONS

Daniel Hayoz et al., "Conduit Artery Compliance and Distensibility Are Not Necessarily Reduced in Hypertension", *Hypertension*, vol. 20, No. 1, Jul., 1992, pp. 1–6.

S. Laurent et al., "Opposite Effects of Ageing on Distal and Proximal Large Arteries in Hypertensives" from a Workshop of the International Society of Hypertension and Arterial Compliance, Mar. 3–7, 1992, Paris, France.

M. J. Mulvany, "A Reduced Elastic Modulus of Vascular Wall Components in Hypertension?", *Hypertension*, vol. 20, No. 1, Jul., 1992, pp. 7–8 and 11.

Raffaele DeCesaris et al., "Large Artery Compliance in Essential Hypertension: Effects of Calcium Antagonism and β–Blocking", *American Journal of Hypertension, Inc.*, vol. 5, No. 9, Sep., 1992, pp. 624–628.

Thomas B. Watt, Jr. and Charles S. Burrus, "Arterial Pressure Contour Analysis for Estimating Human Vascular Properties", *Journal of Applied Physiology*, vol. 40, pp. 171–176.

Howard A. Schwid et al., "Computer Model Analysis of the Radial Artery Pressure Waveform", *Journal of Clinical Monitoring*, vol. 3, No. 4, Oct., 1987, pp. 220–228.

Alain Simon et al., "Haemodynamic Basis of Early Modifications of the Large Arteries in Borderline Hypertension", *Journal of Hypertension*, vol. 5, No. 2, 1987, pp. 179–184.

A.C. Simon et al., "An Evaluation of Large Arteries Compliance in Man", *American Journal of Physiology*, vol. 237, No. 5, 1979, pp. H550–H554.

Gary E. McVeigh et al., "Reduced Vascular Compliance as a Marker for Essential Hypertension", *American Journal of Hypertension*, vol. 4, No. 3, Part 1, Mar., 1991, pp. 245–251.

Zhaorong Liu et al., "Estimation of Total Arterial Compliance: An Improved Method and Evaluation of Current Methods", *American Physiological Society*, 1986, pp. H588–H600.

W. J. Stok et al., "Noninvasive Cardiac Output measurement by Arterial Pulse Analysis Compared with Inert Gas Rebreathing", *American Physiological Society*, 1993, pp. 2687–2693.

S. Aakhus et al., "Non–Invasive Estimates of Aortic Root Pressures: External Subclavian Arterial Pulse Tracing Calibrated by Oscillometrically Determined Brachial Arterial Pressures", *Clinical Physiology*, vol. 13, 1993, pp. 573–586.

*Primary Examiner*—John P. Lacyk
*Attorney, Agent, or Firm*—E. Victor Indiano

[57] ABSTRACT

A method is disclosed for diagnosing, monitoring and treating cardiovascular pathologies. Among the hemodynamic parameters of interest are peripheral resistance, compliance, and cardiac (left ventricular) output. Peripheral resistance determined according to the present invention has been found to be a reliable indicator, not only of hypertension, but also of the cause of the hypertension. The determined peripheral resistance can be compared against a predetermined threshold value. This comparison helps to foster a diagnosis of a hypertensive condition.

9 Claims, 9 Drawing Sheets

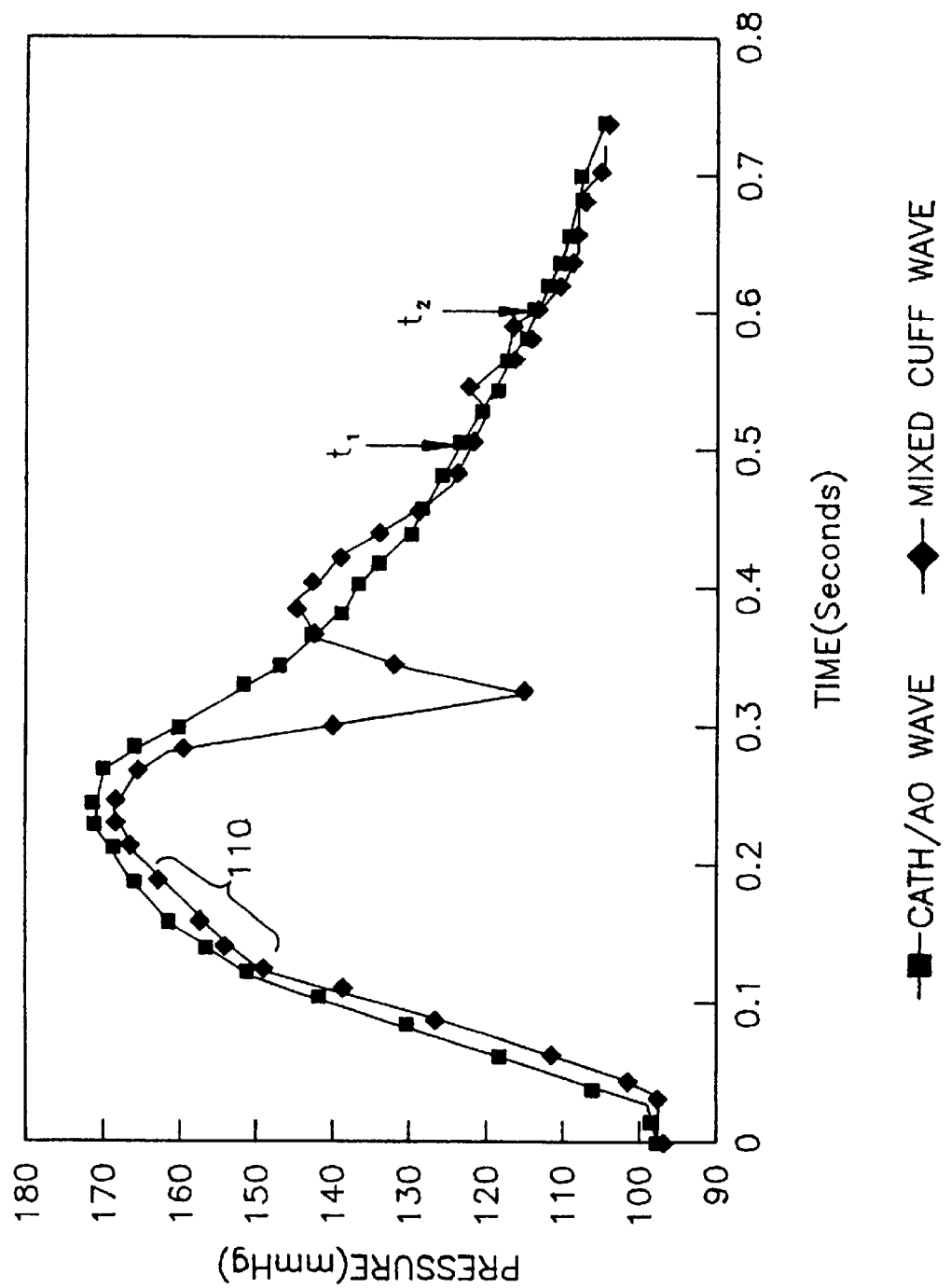

METHOD FOR DIAGNOSING, MONITORING AND TREATING HYPERTENSION AND OTHER CARDIAC PROBLEMS

This is a division of application Ser. No. 08/169,590, filed Dec. 17, 1993, now U.S. Pat. No. 5,836,884.

TECHNICAL FIELD OF THE INVENTION

The present invention relates to a method for diagnosing, monitoring and treating cardiovascular pathologies, and more particularly to a method of determining hemodynamic parameters in a human cardiovascular system by analyzing arterial waveforms, methods for using the parameters so determined for diagnosing hypertension and other cardiovascular problems and diseases, and devices that incorporate the methods of the present invention.

BACKGROUND OF THE INVENTION

Cardiovascular disease is a leading cause of death and disability. One cardiovascular disease that affects a large number of people is hypertension, which is defined as abnormally elevated blood pressure. Hypertension is quite common. It is estimated that over 60,000,000 Americans suffer from hypertension.

To prevent cardiac disorders from causing death, serious illness and disability, it is important to monitor the condition of a person's cardiovascular system, and to analyze the data from the monitoring so performed to determine whether any pathologies exist in the person's cardiovascular system that should be treated to prevent further degradation of the patient's cardiovascular system.

The method used most often to monitor a cardiovascular condition is the determination of the blood pressure of the patient. Human blood pressure is normally described by systolic and diastolic pressure readings, which are usually given in millimeters of mercury (mmHg). The systolic pressure is the higher of the two values given, and the diastolic pressure is the lower of the two values given. From a physiologic standpoint, the systolic pressure usually represents that pressure at which blood begins flowing through an artery that is compressed by a blood pressure cuff during a blood pressure measurement. At pressures above the systolic pressure (supra-systolic pressures) the flow of blood through the artery is blocked by the blood pressure cuff used to take the blood pressure reading. The diastolic pressure is that pressure below which the blood flow through the artery is unimpeded by the blood pressure cuff. A further explanation of the physiologic basis of the systolic and diastolic blood pressure readings can be found in Chio, U.S. Pat. No. 4,880,013, that issued on Nov. 14, 1989, and Chio U.S. Pat. No. 5,162,991, that issued on Nov. 10, 1992. The Chio '013 and '991 patents were invented by the Applicant, and are assigned to the assignee of this application.

It is generally accepted that a systolic blood pressure reading of greater than 140 mmHg, and/or a diastolic blood pressure reading of greater than 90 mmHg is indicative of a hypertensive condition. These pressure readings are generally considered to be indicative of hypertension, regardless of whether these blood pressure readings are made by non-invasive or invasive blood pressure determination methods.

Although systolic blood pressure and diastolic blood pressure readings are useful for determining whether hypertension exists, they are not completely reliable. The systolic/diastolic hypertension threshold (140 mmHg/90 mmHg) line of demarcation does not always provide a completely accurate guide for determining either which patients are hypertensive, or what factors caused the hypertension. In this regard, it is believed that approximately 80% of hypertension cases are categorized as "essential hypertension." A diagnosis of "essential hypertension" usually means that the causes of the hypertension are unknown. As such, these persons having "essential hypertension" may not be diagnosed accurately and reliably by only measuring the patient's systolic and diastolic pressures. For example, a patient may have a measured systolic and diastolic pressure of less than 140 (systolic)/90 (diastolic), but still may be genetically hypertensive. Conversely, a person may have a measured systolic/diastolic blood pressure of greater than 140/90, but may be not hypertensive either through environment, or genetic causes. Most importantly, it is difficult, if not impossible for a physician to treat a patient's hypertension properly if the physician does not know the cause of the hypertension.

For more than twenty years, studies have been conducted to find other physiological hemodynamic parameters in addition to systolic and diastolic blood pressure readings. For example, in the mid-1970's, Watt performed studies that tried to evaluate the "compliance" or "elasticity" of an artery. Watt, T. B. at et al., *Arterial Pressure Contour Analysis for Estimating Human Vascular Properties, J. Applied Physics,* (1976); at pages 171–176. In Watt's study, he used an electrical circuitry model, and a Windkessel model that were modified for a human arterial system to make his model for determining physiological and hemodynamic parameters. Watt's model defined two compliance components, $C_1$ and $C_2$, a Resistance, R and an Inductance, L. By using equations that had their genesis in the electrical circuitry art area, Watt further defined that $C_1$ was the elastic compliance of major or large arteries. This factor ($C_1$) was also called "proximal compliance." Watt found that $C_2$ is the compliance of the smaller peripheral arteries, which is also referred to as "distal compliance."

Watt reported that correlations existed between the value of the proximal compliance ($C_1$) and the distal compliance ($C_2$) and the existence of hypertension. Primarily, Watt found that hypertensive patients tended to have smaller compliance values ($C_1$ and $C_2$). Since Watt's study, many other studies have been conducted that were focused on the arterial compliances and their relations to various causes of hypertension. Many groups have reported the relationship between proximal compliance ($C_1$) and hypertension. In U.S. Pat. No. 5,054,493, which issued Oct. 8, 1991, J. N. Cohn, et al. reported his findings that distal compliance ($C_2$) is more sensitive than proximal compliance ($C_1$) for determining hypertension. Cohn therefore suggested that distal compliance ($C_2$) was a better parameter for diagnosing hypertension than proximal compliance ($C_1$). Cohn is also worth reviewing for its discussion of the Windkessel model, and its citation of a large number of references dealing with studies relating to compliance. At column 3, Cohn cites a larger number of studies conducted on the properties of the large proximal arteries, and the relationship of the properties of these arteries (in particular their compliance ($C_1$)) to hypertension.

Since $C_2$ is the distal compliance, and since distal compliance is strongly influenced by the reflection wave from the peripheral arteries in the arterial system, its measurement may need to be performed either by an invasive method, or alternately by a very sensitive non-invasive sensing device. An extremely sensitive non-invasive sensing device is probably necessary in order to obtain a near-perfect wave of the type that is typically found when using invasive techniques. This reflection phenomenon and its impact on its measurement was reported by Schwid, in Schwid, H. A., et al., *Computer Model Analysis of Radial Artery Pressure Waveforms, J. Clinical Monitoring* (1987), Vol. 3, No. 4, at pages 220–228. Additionally, the measurement of distal compliance ($C_2$) may also be affected by the reflection wave. Further, the measurement of distal compliance may have fluctuations caused by other human factors, such as fluctuations in the arterial cross-section area and arterial blockage at the measured limb. As such, distal compliance $C_2$ is still not a very reliable parameter for determining the physical conditions of a human cardiovascular system and other hemodynamic parameters. A recent study by Hayoz suggests that compliance may not be a valid indicia of hypertension, as Hayoz's study found that the elastic behavior (compliance) was not necessarily altered by an increase in blood pressure. See, Hayoz, D. et al., *Conduit Artery Compliance and Distensibility are Not Necessarily Reduced in Hypertension, Hypertension* 1992, Vol. 20, at pages 1–6.

Although the references cited above all relate to methods for determining cardiac and cardiovascular condition, and some of the methods discussed above relate to hemodynamic parameters other than the determination of systolic and diastolic pressure, room for improvement exists.

It is therefore one object of the present invention to provide an improved method for determining hemodynamic parameters in a human cardiovascular system.

SUMMARY OF THE INVENTION

In accordance with the present invention, a method is provided for diagnosing a cardiovascular pathology in a patient. The method comprises the steps of (1) gathering cardiovascular condition information from the patient, and (2) determining the patient's systolic, diastolic and mean arterial pressures from the gathered cardiovascular condition information. At least one of the determined diastolic, systolic and mean arterial pressures is used to determine the patient's peripheral resistance. The determined peripheral resistance is then compared to a predetermined peripheral resistance threshold value. The patient is then diagnosed as having a cardiovascular pathology if the patient's determined peripheral resistance exceeds the predetermined peripheral resistance threshold value.

In a preferred embodiment of the present invention, the method further comprises the steps of using at least one of the determined diastolic, systolic and mean arterial pressures to determine the patient's cardiac output. The determined cardiac output is then compared to a predetermined threshold value. The patient is diagnosed as hypertensive if the product of the patient's cardiac output and peripheral resistance exceeds the predetermined threshold value. Preferably, the predetermined threshold value against which the determined product of cardiac output and peripheral resistance is compared is a predetermined mean arterial pressure threshold value, i.e. MAP=(CO)(PR).

Also in accordance with the present invention, a method is provided for diagnosing a patient as being at risk for having a cardiovascular pathology. This method comprises the steps of affixing a non-invasive pressure inducing means and transducer means to a patient. The pressure induced by the pressure inducing means is elevated to a supra-systolic pressure, and is then decreased over time to a sub-diastolic pressure. A data stream is obtained from the transducer means. The data stream includes pressure data and pulsation signal data, to obtain a series of pulsation signal data waveforms. The waveforms include at least pulsation signal data taken at a supra-systolic pressure, and pulsation signal data taken at a sub-diastolic pressure. A pseudo-aortic wave contour is created from the obtained supra-systolic waveform data and the sub-diastolic waveform data. The patient is then diagnosed as having a cardiovascular pathology by comparing the pseudo-aortic wave contour to cardiovascular contours exhibiting known cardiovascular pathologies.

Further in accordance with the present invention, a method is provided for diagnosing a patient as being at risk for having a cardiovascular pathology. This method comprises the steps of affixing a non-invasive pressure inducing means and transducer means to the patient. The pressure induced by the pressure inducing means is then elevated to a supra-systolic pressure. The pressure induced by the pressure inducing means is then decreased over time to sub-diastolic pressure. A data stream is obtained from the transducer means. The data stream includes pressure data and pulsation signal data, to obtain a series of pulsation signal data waveforms. The waveforms include at least pulsation signal data taken at a supra-systolic pressure, and pulsation signal data taken at a sub-diastolic pressure. The peak cardiac contractility is then determined from the data stream so obtained. The patient can then be diagnosed as having a cardiovascular pathology based on the determined peak cardiac contractility.

Additionally, in accordance with the invention, methods are disclosed for determining peripheral resistance, diastolic flow velocity, left ventricle contractility, and the compliance of the artery. Further, the invention comprises an apparatus for determining these parameters.

One feature of the present invention is that a wide range of hemodynamic parameters can be determined through non-invasive means. Many of the parameters discovered by the Applicant, and disclosed in connection with this invention were not heretofore either obtainable, or recognized as being useful for diagnosing cardiovascular pathologies. Further, some of the parameters of the present invention were formerly obtainable only through an invasive procedure that usually involved catheterizing the patient. The Applicant's invention improves upon these prior invasive techniques, by enabling the practitioner to have access to a greater array of data without requiring the patient to go through the discomfort and expense associated with invasive procedures.

A further feature of the present invention is that it provides a method for analyzing arterial pulse waveforms which can be measured from non-invasive cuff pulse waves to derive hemodynamic parameters, such as diastolic flow velocity, peripheral resistance, compliance, or elastic constant of an artery, and cardiac (left ventricle (LV)) contractility.

Another feature of the present invention is that the applicant has found that the peripheral resistance derived from the diastolic flow velocity is a better method for diagnosing hypertension than using compliance. The cardiac (LV) contractility obtained by the applicants' technique of using non-invasive means is useful for determining not only hypertension, but certain other cardiac problems and irregularities.

These and other features will become apparent to those skilled in the art upon a review of the detailed description of a preferred embodiment of the present invention presented below, in conjunction with the drawings presented herewith.

BRIEF DESCRIPTION OF THE DRAWINGS

FIG. 12A is a graphical representation of a pseudo-aortic cuff wave plotted against an actual aortic pressure wave taken from an invasive catheter, illustrating an aortic stenosis cardiovascular pathology;

DETAILED DESCRIPTION OF THE INVENTION

I. Overview

Figure 1:
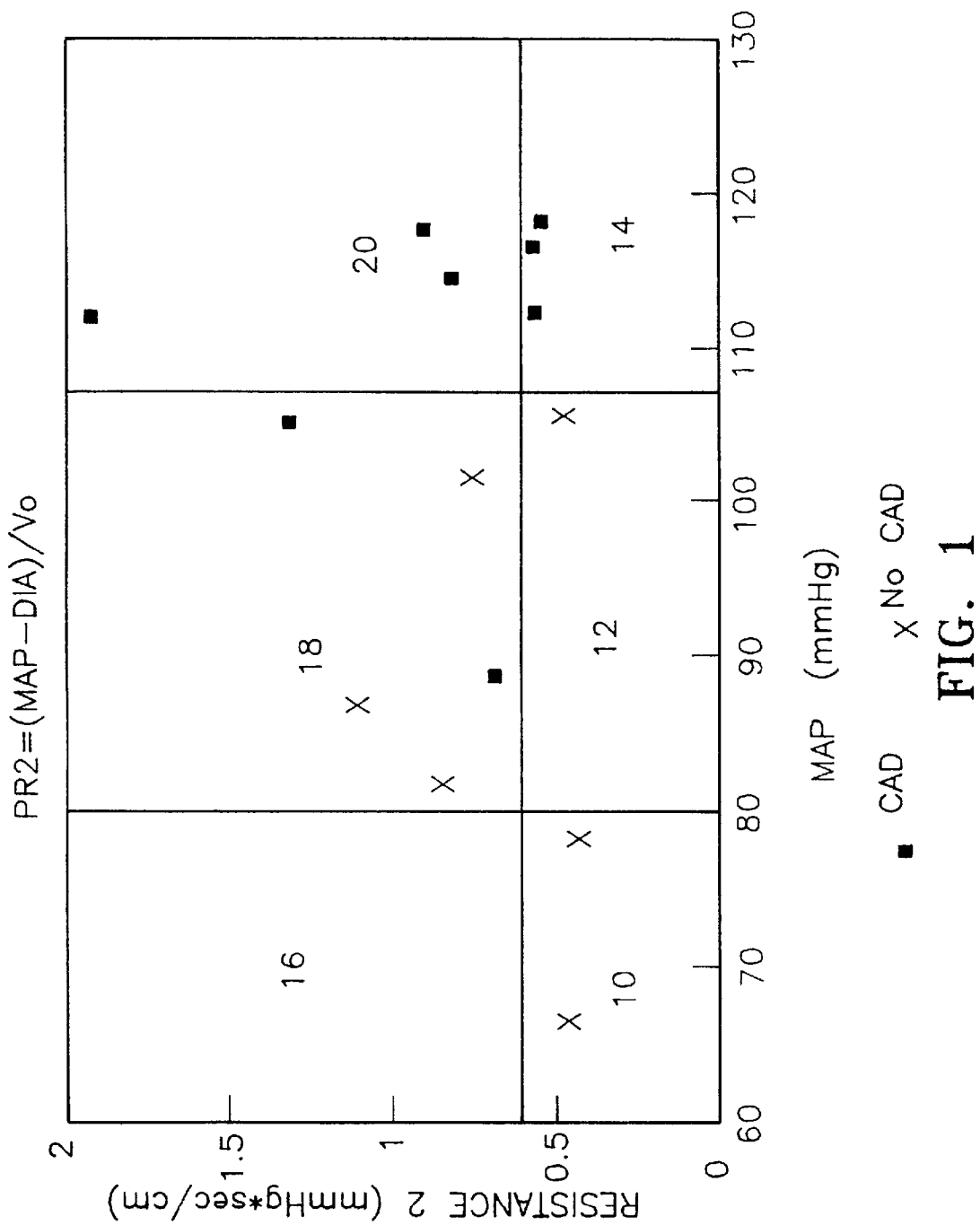
FIG. 1 is a graphical representation showing the results of the study conducted of 14 subjects, wherein derived distal peripheral resistance (PR$_2$) was plotted as a function of mean arterial pressure (MAP)

Analyzing an arterial pressure or pulse waveform to derive certain important parameters, such as arterial compliance or elasticity constants, arterial blood flow or velocity, and peripheral resistance, as well as cardiac output and contractility are used in the present invention for diagnosing a wide array of cardiovascular pathologies, including complications and disorders, and especially for diagnosing essential hypertension.

One direct method for obtaining the above hemodynamic parameters, and in particular the arterial characteristics, is by using an ultrasonic echo technique. By the use of an ultrasonic echo technique, one may measure the pulse wave velocity and diameter of an artery. From these measured parameters, one can then use calculations to determine the compliance and blood flow. An indirect method for determining certain of these parameters is by fitting the arterial wave (an invasive catheterization wave) to an electrical model known as the Windkessel model. To do this, one must assume that capacitance equals compliance; electrical resistance equals peripheral resistance; and conductance equals inertia. However, for an arterial pulse waveform obtained by a non-invasive method (such as from an inflated cuff, pressure array and optical absorption, or reflection sensors) that provide waveforms different from those obtained from invasive catheterization wave, there is no well-defined method for obtaining the hemodynamic parameters. In this regard, it should be noted that cardiac parameters, cardiac output, and contractility are normally measured by an invasive catheterization method.

As described in greater detail in Chio U.S. Pat. No. 4,880,013, invasive measurement techniques are generally more disruptive and more expensive than non-invasive techniques. When possible, practitioners prefer to use non-invasive techniques to measure blood pressure parameters, as they cause less trauma to the patient. Therefore an ability to measure cardiac parameters by a non-invasive technique is preferred to an invasive technique.

The Chio '013 patent describes in detail the methodology for obtaining arterial pulse waveforms. The present invention analyzes these waveforms, to use these waveforms to derive hemodynamic parameters, such as diastolic flow velocity, peripheral resistance, arterial (distal) and aortic (proximal) compliances, and elastic constants. Additionally, the present invention uses the Chio waveforms to derive cardiac (left ventricle) contractility. However, the methods described in this application may also be used with waveforms other than those derived by the Chio method. For example, the analysis methods of the present invention may be useful when applied to waveforms measured by other invasive, or even other non-invasive sensing devices.

The applicant has discovered that both distal and proximal arterial compliances are dependent on the cross-sectional areas of the arteries. However, the diastolic flow velocity is independent of the size of the arteries. Hypertension is directly related to the Peripheral Resistance (PR) of a cardiovascular system, and blood flow velocity (VO) is intrinsically dependent upon the resistance in a manner described by the equation below.

VO=(Pressure In−Pressure Out)÷Peripheral Resistance

Therefore, two relative peripheral resistance parameters, PR$_1$ and PR$_2$, may be defined as follows:

$$PR_1 = \frac{\text{Systolic Pressure} - \text{Diastolic Pressure}}{V_o} \qquad \text{Eqn. 58}$$

and $$PR_2 = \frac{\text{Mean Arterial Pressure} - \text{Diastolic Pressure}}{V_o} \qquad \text{Eqn. 59}$$

where (Systolic Pressure−Diastolic Pressure)=Pulse Pressure (PP); and V$_o$ equals the blood flow velocity.

The applicant has found that a measurement of the diastolic flow velocity (as defined in this application), the defined relative peripheral resistances (PR$_1$ and PR$_2$), or some combination of the flow velocity and peripheral resistance serve as better indices or markers for diagnosing hypertension than the use of a measurement of compliance. These values are believed to be especially useful in determining both essential hypertension and in hypertension cases in persons having a normal cardiac output. The instant invention's use of parameters other than compliance and distensibility to help diagnose hypertension are believed to be most useful, and represent a substantial leap forward in the art, especially in view of recent studies which indicate that compliance and distensibility may not be reduced in hypertensive patients. See, Hayoz et al., supra.

The present invention also uses the relative peripheral resistance (as defined above) as a marker or index for diagnosing hypertension, and for providing guides for methods for treatment by hypertension.

Experimental studies undertaken by the applicant also support the applicant's claim that relative peripheral resistance can be used as a marker or index for diagnosing hypertension, and for providing methods for treatment of hypertension.

FIG. 1 is a graph showing the results of a study conducted of 14 subjects, wherein derived distal peripheral resistance ($PR_2$) was plotted as a function of mean arterial pressure (MAP). The graph is then divided into six sections, 10, 12, 14, 16, 18, 20. These six sections correspond to six different patient conditions. In reviewing these sections, it should be noted that these sections cannot only be related to mean arterial pressure (MAP), and peripheral resistance ($PR_2$), but also to cardiac output. This chart can be used as an indication of cardiac output, as cardiac output is generally equal to mean arterial pressure, divided by peripheral resistance, as expressed by the equation $$\frac{MAP}{PR} = CO$$

Section 10 represents those patients having a normal peripheral resistance (PR), and a normal to low mean arterial pressure (MAP). Because of these conditions, these patients within Section 10 are those patients whose cardiac outputs (CO) are in the low-normal range. Section 12 represents those patients having a normal peripheral resistance, and normal mean arterial pressure. The patients of Section 12 also have a normal cardiac output.

Section 14 represents those patients having a low peripheral resistance and a high mean arterial pressure. As such, the patients of Section 14 have a high cardiac output. Section 16 represents those patients having a high peripheral resistance and a low mean arterial pressure. As such, these patients have a low cardiac output.

Section 18 represents those patients having a high peripheral resistance and a normal mean arterial pressure. As such, the patients of Section 18 have a low cardiac output. Section 20 represents those patients having a high peripheral resistance and a high mean arterial pressure. These patients may have a cardiac output that is either normal or high.

As used in these discussions, a high peripheral resistance is generally one above 0.6 (mmHg) (sec/cm). Further, a high mean arterial pressure is generally above 108 mmHg, a low mean arterial pressure is generally below 80 mmHg, and a normal mean arterial pressure is between 80 and about 108 mmHg.

An analysis of FIG. 1 will reveal one of the applicant's novel methods for determining and diagnosing hypertension. Those patients who fall within Section 20 are those persons who are very likely to have a high peripheral resistance type hypertension. Those patients who fall within Section 14 are those persons who more likely have a high cardiac output type hypertension. Persons having high blood pressure hypertension, either caused by high peripheral resistance or by high cardiac output, are at a higher risk of having a stroke or heart attack than those not having hypertension. By determining the cause of the hypertension (either caused by high peripheral resistance or a high cardiac output), the physician is better able to plan an appropriate treatment to correct the patient's hypertensive condition. For example, a hypertensive person (or those with high blood pressure) who have a high peripheral resistance can usually be treated with a vaso-dilator. However, those persons with the high cardiac output are preferably treated with calcium channel blockers.

Substantiation of the invention is also provided in FIG. 1. It will be noted that 8 of the 14 catheterization patients whose results are represented in FIG. 1 were confirmed to have coronary artery disease (CAD). FIG. 1 also indicates that all 6 hypertensive patients having either a high peripheral resistance or a high cardiac output (those in Sections 14 and 20 respectively) have coronary artery disease. However, those normotensive patients having a normal mean arterial pressure, and a high peripheral resistance (those in Section 18) also have a certain risk of having coronary artery disease. Persons with a normal mean arterial pressure and a low peripheral resistance (those in Sections 10 and 12) generally are shown to have a lower risk of coronary artery disease, as indicated in this study. Thus, the data of FIG. 1 supports the Applicant's thesis that certain parameters, such as peripheral resistance, mean arterial pressure, and cardiac output can be used as guidelines for diagnosing hypertension and other cardiac diseases. Additionally, as discussed above, peripheral resistance, mean arterial pressure and cardiac output measurements can be used to help diagnose the source of the person's hypertensive condition, and can thereby better facilitate treatment of the patient's condition.

The present invention also describes the method of deriving the cardiac (left ventricle (LV)) contractility. Normally, cardiac (LV) contractility is only obtainable through an invasive catheterization measurement. With the method of the present invention, cardiac (LV) contractility can be measured using non-invasive cuff pressure waveforms. This cardiac (LV) contractility parameter can be used for diagnosing certain other cardiac problems. The present invention's method for deriving cardiac (LV) contractility seems to be relatively reliable. In two clinical studies conducted by the applicant, cardiac contractilities of 968 and 1015 mmHg/second were obtained using the method of the present invention, which compared favorably, and generally similarly to measurements of 1057, and 1000, mmHg/second (respectively) measured by invasive catheterization. In the present invention, a Gaussian curve is used for the calculation of cardiac contractility from a reconstructed aortic wave or supra-systolic cuff wave. However, other curve fitting methods may also be used with this concept, and are within the scope of the present invention.

II. The Physics and Physiology Underlying the Present Invention

A. The Physics

An artery is a generally flexible tube whose interior is filled with blood. The flexible filled tube-like nature of an artery allows an artery to exhibit radial motion, expansion, and compression in a direction generally perpendicular to its wall. This radial motion, expansion and compression are generally in response to blood pressure (P(x,t)). The blood pressure within an artery is generally not constant, but rather changes constantly over time.

Figure 2:
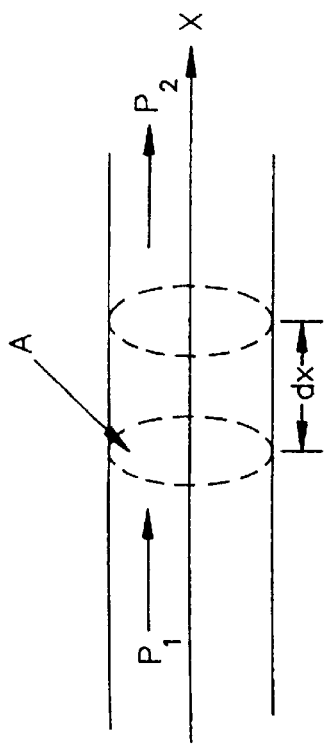
FIG. 2 is a schematic representation of a segment of an artery.

To better understand the impact of a blood pressure on the motion, expansion and compression of an artery, your attention is now directed to FIG. 2. In FIG. 2, ($P_1-P_2$)=dP, which is the pressure difference inside the artery segment, which is itself a function of both time and space (dP(x,t)). The volume of the arterial segment is defined as dV=(A) (dx); and "A" is the cross-section of the artery. As will be appreciated, both the volume of the artery (V) and the cross-sectional area of the artery (A) are functions of time and space. One must further assume an elastic constant (Ke) of the artery, so that its elasticity characteristics can be defined as follows:

$$dP(x,t)=[Ke][dV(x,t)]=Ke[A(x,t)][dx] \quad \text{Eqn. 1}$$

The compliance (C) of an artery can be defined as $$C = \frac{1}{Ke} = \frac{dV}{dP} \quad \text{Eqn. 2}$$

When measurements are taken by a blood pressure cuff, the cuff will generally have a defined effective length ($l_{cuff}$), and a negligible constant of elasticity. In such a case, the pressure or volume variation curve is the integration of the elasticity characteristic equation (Eqn. 1) over the length of the cuff ($l_{cuff}$). The result is the Cuff Pulse Waveform of pressure, as a function of the effective length of the cuff ($l_{cuff}$), at a particular time, t, set forth as follows:

$$P(l_{cuff},t)=Ke[A(t)][l_{cuff}] \quad \text{Eqn. 3}$$

The first derivative of the cuff pulse waveform is as follows:

$$\frac{dP(l_{cuff},t)}{dt} = Ke\left[\frac{dA(t)}{dt}\right][l_{cuff}] \quad \text{Eqn. 4}$$

In order to solve the above equation, and to derive the elasticity constant (Ke), one may assume that a simple sinusoidal pulse wave exists for both the pressure at a particular time ($P_t$), and the cross-sectional area of the artery at a particular time ($A_{(t)}$) in Eqn. 4, where the maximum and minimum change in pressure over time (dP/dt) and change in cross-sectional area over time (dA/dt) should occur at the "zero" point, where the arterial pressure is at its mean value, or the mean arterial pressure (MAP), and the arterial's cross-section is at its mean value ($A_o$). By making these two assumptions, the following equations become true:

$$\left(\frac{dP}{dt}\right)_{max} = Ke\left[\left(\frac{dA}{dt}\right)_{max}\right][l_{cuff}] \quad \text{Eqn. 5}$$

$$\left(\frac{dp}{dt}\right)_{min} = Ke\left[\left(\frac{dA}{dt}\right)_{min}\right][l_{cuff}] \quad \text{Eqn. 6}$$

Figure 3:
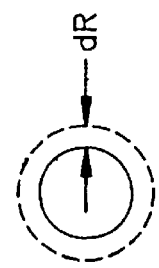
FIG. 3 is a schematic, sectional view of an artery.

In an ideal case, wherein there exists a sinusoidal pulse wave that is only negligibly influenced by external forces (such as when the cuff pressure is at a pressure less than the patient's diastolic pressure), the cross-sectional variation ($dA_{(t)}$), can be defined from a sketch shown in FIG. 3. The sketch in FIG. 3 suggests that change in area equals $2\pi R$ times the change in radius, as represented by the following equation:

$$dA=[2\pi R][dR] \quad \text{Eqn. 7}$$

In this equation, R equals the radius of the artery. From this equation it will be appreciated that the change in the area of the artery over time can be represented by the following equation:

$$\frac{dA}{dt} = [2\pi R]\left[\frac{dR}{dt}\right] \quad \text{Eqn. 8}$$

If one assumes that the radius of the artery at any particular time ($R_{(t)}$) is a function of the mean radius and the frequency of the pulse, the following equation applies:

$$R_t=R_o[\sin(2\pi ft)] \quad \text{Eqn. 9}$$

where "f" equals the frequency of the pulse. Therefore, the maximum change in radius "R" over time can be represented by the following equation:

$$\left(\frac{dR}{dt}\right)_{max} = R_o[f][\cos(o)] = R_o[2\pi f] \quad \text{Eqn. 10}$$

Similarly, the minimum change in radius "R" over time can be represented by the following equation:

$$\left(\frac{dR}{dt}\right)_{min} = -R_o[2\pi f] \quad \text{Eqn. 11}$$

so that the following equation applies:

$$\left[\left(\frac{dR}{dt}\right)_{max} - \left(\frac{dR}{dt}\right)_{min}\right] = 2R_o[2\pi f] = 4\pi[R_o][f] \quad \text{Eqn. 12}$$

and that therefore $$\left(\frac{dA}{dt}\right)_{max} - \left(\frac{dA}{dt}\right)_{min} = [8\pi^2][R_o^2][f] \quad \text{Eqn. 13}$$

The pulse frequency, (f), equals $\frac{1}{2}T_{pp}$, where $T_{pp}$ may be defined as the peak-to-peak width, that is the time period between the peak positive slope $(dP/dt)_{max}$ and the peak negative slope $(dP/dt)_{min}$. Your attention is directed to FIG. 4 which shows an arterial pulse wave, wherein the peak positive slope $(dP/dt)_{max}$ and the peak minimum slope $(dP/dt)_{min}$ are indicated. Therefore, the peak-to-peak value of the maximum, or positive slope (or change in pressure over time, $(dP/dt)_{max}$)) and the minimum, (or negative slope or change in pressure over time, $(dP/dt)_{min}$)) which equals the change in the pressure slope pressure over time, (dP/dt)$_{pp}$, can be obtained through the following equations.

$$\left(\frac{dP}{dt}\right)_{pp} = \left(\frac{dP}{dt}\right)_{max} - \left(\frac{dP}{dt}\right)_{min} = \quad \text{Eqn. 14}$$

$$= Ke\left[\left(\frac{dA}{dt}\right)_{max} - \left(\frac{dA}{dt}\right)_{min}\right][l_{cuff}] \quad \text{Eqn. 15}$$

$$= Ke[8\pi^2][R_o^2][f][l_{cuff}] = [8\pi][Ke][A_o][l_{cuff}][f] \quad \text{Eqn. 16}$$

$$= \frac{8\pi[Ke][A_o][l_{cuff}]}{2T_{pp}} \quad \text{Eqn. 17}$$

$$= \frac{4\pi[Ke][A_o][l_{cuff}]}{T_{pp}} \quad \text{Eqn. 18}$$

In the above equations $$A_o = \pi(R_o)^2 \qquad \text{Eqn. 19}$$

which each equal the mean cross-sectional area "A" of the artery. The elasticity constant, Ke can be determined as follows:

$$Ke = \left(\frac{dP}{dt}\right)_{pp} \div 8\pi \div f \div A_o \div l_{cuff} \qquad \text{Eqn. 20}$$

$$= \left(\frac{dP}{dt}\right)_{pp} [T_{pp}] \div 4\pi \div A_o \div l_{cuff} \qquad \text{Eqn. 21}$$

Further, the compliance (C) can be obtained as follow:

$$C = \frac{1}{Ke} = \frac{(8\pi)(A_o)(l_{cuff})(f)}{\left(\frac{dP}{dt}\right)_{pp}} \qquad \text{Eqn. 22}$$

$$= (4\pi)(A_o)(l_{cuff}) \div T_{pp} \div \left(\frac{dP}{dt}\right)_{pp} \qquad \text{Eqn. 23}$$

In the case of a non-sinusoidal pulse waveform, $$f = \left(\frac{1}{2}\right)(T_{pp}) \qquad \text{Eqn. 24}$$

Additionally, $T_{pp}$ should be used to calculate both the elasticity constant (Ke) and the compliance (C).

In a real human cardiovascular system, since the pulse waveform is not a sinusoidal function, the systolic cycle, Systolic Wave SW, and diastolic cycle, Diastolic Wave (DW), may be treated independently. As such, the cuff pulse waveform derived in Eqn. 4 for determining the elasticity constant (Ke) and compliance (C) may only be valid for the systolic wave (SW). Therefore, the use of ½ the peak-to-peak width (½$T_{pp}$) as the frequency of the systolic wave (SW) is suggested.

Figure 4:
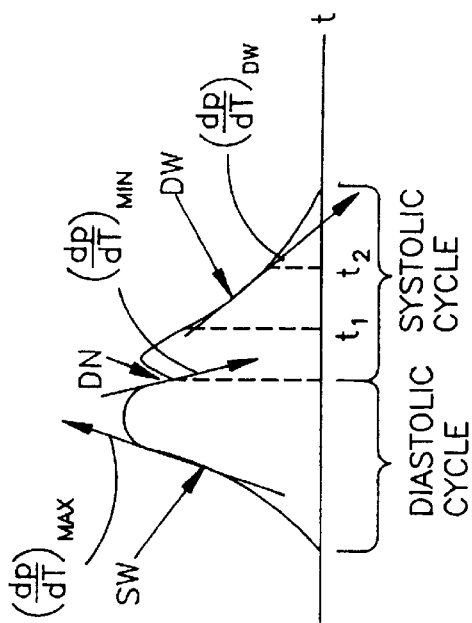
FIG. 4 is a schematic representation of an arterial pulse wave showing the systolic cycle and diastolic cycle; the peak positive slope and the peak negative slope of the systolic cycle, and the diastolic slope of the diastolic cycle.

The diastolic wave (DW) begins after the end of the systolic cycle (SW). The diastolic wave (DW) begins at the "dicrotic notch" which is observed by an invasive catheter measured arterial pulse waveform as shown in FIG. 4. As shown in FIG. 4, the dicrotic notch (DN) is generally used as the line of demarcation between the systolic cycle and the diastolic cycle.

The equation of motion of this diastolic wave (DW) may be described by Eqn. 1, above, so long as one assumes that at the location of the catheter tip ($x_1$), the pulse waveform can be defined as follows:

$$\frac{dP_{(xl,t)}}{dt} = Ke[A_{(xl,t)}]\left[\left(\frac{dx}{dt}\right)\right]_{xl} \qquad \text{Eqn. 25}$$

$$= Ke[A_{(xl,t)}][V_1] \qquad \text{Eqn. 26}$$

where $$V_1 = \left(\frac{dx}{dt}\right)_{xl} \qquad \text{Eqn. 26A}$$

One can also make two other assumptions. The first assumption is that an almost linear pressure decrease of a pulse pressure occurs from a point in the pulse cycle beginning at around the mean value (which is the mean arterial pressure (MAP) of the pulse wave) to the end of the diastolic cycle. Turning now to FIG. 4, this area is shown as the section of the pulse wave which begins at the dicrotic notch (DN) to the end diastolic point. A second assumption is that due to second and higher order harmonics in the diastolic wave, DW causing negligible oscillation, the slope (dP/dt)DW of this near-linear diastolic wave (as shown in FIG. 4) may be obtained from the diastolic wave (DW) at times $t_1$ and $t_2$ according to the following equations:

$$\left(\frac{dP}{dt}\right)DW = \frac{P_{(xl,t2)} - P_{(xl,t1)}}{(t2 - t1)} \qquad \text{Eqn. 27}$$

$$= Ke[A_o][V_o] \qquad \text{Eqn. 28}$$

where $A_o$ equals the mean cross-section area of the artery, and $V_o$ equals the mean blood flow velocity occurring during the diastolic wave DW.

From Eqn. 21, we have obtained the following relationships:

$$(Ke)(A_o) = \left[\left(\frac{dP}{dt}\right)_{pp}\right][T_{pp}] \div 4\pi \div l_{cuff} \qquad \text{Eqn. 29}$$

$$\left(\frac{dP}{dt}\right)_{DW} = \left(\frac{dP}{dt}\right)_{pp}[T_{pp}][V_o] \div 4\pi \div l_{cuff} \qquad \text{Eqn. 30}$$

$$V_o = \left[\frac{(4\pi)(l_{cuff})}{T_{pp}}\right]\left[\frac{\left(\frac{dP}{dt}\right)_{DW}}{\left(\frac{dP}{dt}\right)_{pp}}\right] \qquad \text{Eqn. 31}$$

where the change in pressure over time of the pulse pressure $$\left(\frac{dP}{dt}\right)_{pp} \qquad \text{Eqn. 32}$$

and the peak-to-peak width ($T_{pp}$) are obtained from the first derivative curve of the systolic wave SW of a cuff pulse waveform, and the change in pressure over time of the diastolic wave $$\left(\frac{dP}{dt}\right)_{DW} \qquad \text{Eqn. 33}$$

is obtained either (a) from the diastolic wave DW of an invasive catheter-measured pulse waveform, or (b) from a cuff pulse waveform that assumes a diastolic wave having a linear slope from the dicrotic notch to the diastolic end point.

B. A Simple Model of the Human Cardiovascular System

Figure 5:
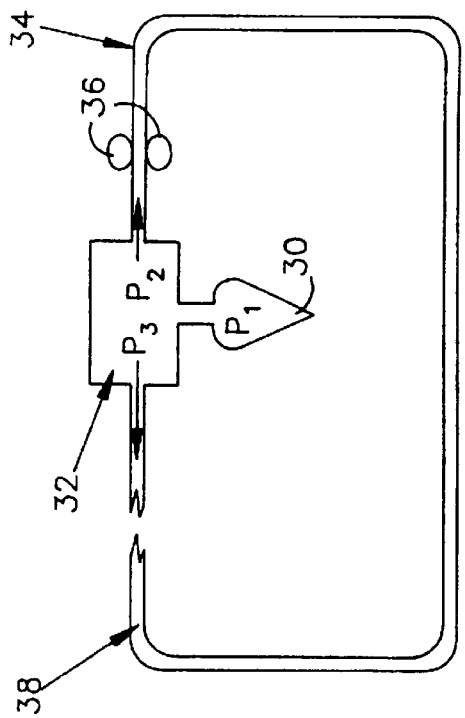
FIG. 5 is a schematic representation of a simple physiological model for the aorta, and the large artery system.

A simple physiological model for the aorta, and the large artery system is schematically represented in FIG. 5. The primary cardiovascular components shown in FIG. 5 include the heart 30, whose left ventricle (LV) pumps blood to the aorta 32. The arteries are represented only as the arterial branch 34 on which the cuff 36 exerts pressure. Normally, this will be the brachial artery. The remainder of the arterial system is represented as artery 38.

FIG. 5 also displays three pressures, $P_1$, $P_2$, and $P_3$. $P_1$ equals the blood pressure from the left ventricle of the heart 30 to the aorta 32. Pressure $P_2$ represents the pressure from the aorta 32 to the artery 34 on which the cuff 36 is exerting pressure; and $P_3$ equals the pressure exerted on the rest of the arterial system 38.

When a catheter tip is placed inside the aorta, the pressure wave inside the aorta ($P_{a(xt)}$), may be defined according to Eqn. 34 below, which is reproduced below. It will be appreciated that Eqn. 34 is generally equivalent to Eqn. 1, above.

$$dP_{a(x,t)} = [Ke_{(aorta)}]dV_{(x,t)} = [Ke_{(aorta)}][dA_{a(t)}][dx] \quad \text{Eqn. 34}$$

Figure 6:
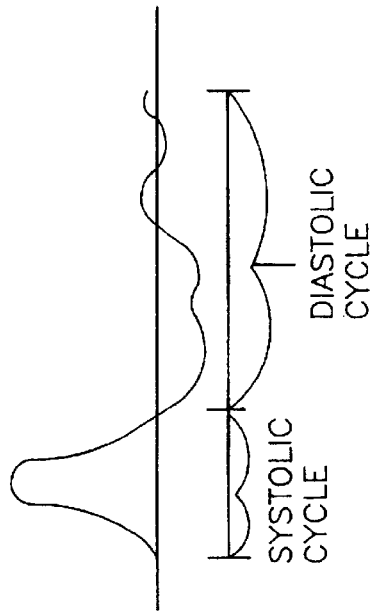
FIG. 6 is a schematic representation of a segment of the aorta.

Where, $P_a$, $Ke_{(aorta)}$ and $A_{a(t)}$ are the pressure wave, elasticity constant, and cross-sectional area, respectively, of the aorta, as shown below in FIG. 6.

If one assumes that the "effective length" of the aorta is shown by "$l_a$," by integration over the effective length ($l_a$) the aortic pressure waveform ($P_{a(xa,t)}$) at aortic location xa may be defined as follows:

$$P_{a(xa,t)} = [Ke_{(aorta)}][A_{a(xa,t)}][l_a] \quad \text{Eqn. 35}$$

It is believed that a typical catheter-measured aortic pressure wave may have an appearance very similar to the wave described above, with the systolic wave SW and the diastolic wave DW separated from each other by a dicrotic notch.

Since a human cardiovascular system is a closed system with its base pressure at diastolic pressure ($P_{dia}$), the aortic pressure $P_{at}$ can be described as $$P_{a(t)} = P_{a(t)l} + P_{dia} \quad \text{Eqn. 35A}$$

where $P_{a(t)l}$ is the pressure rise in the aortic pressure above the diastolic point.

When a cuff is placed on the brachial artery of an arm, and the cuff is inflated to a pressure that exceeds the systolic point, a supra-systolic condition exists. A supra-systolic condition is schematically represented in FIG. 8, which illustrates that the flow of blood through the brachial artery 34 is blocked by the supra-systolic pressure exerted on the brachial artery 34 of the cuff 36. As will be appreciated, a cardiovascular system wherein the brachial artery 34 is at a supra-systolic condition will behave in a manner different from one not at a supra-systolic condition, due to the occlusion of one of the arterial branches 34 (here shown as the brachial artery).

When the pressure wave received by the cuff 36, is at a point where the cuff pressure exceeds the systolic point, a supra-systolic wave ($P_{ss(t)}$) exists, the pressure of which is related to the pressure at the aorta $P_{a(t)}$ by a geometric transformation factor, $G_{ss(t)}$, and a non-geometric artery-cuff coupling factor ($H_{ss(t)}$) as set forth below:

$$P_{ss(t)} = G_{ss(t)}P_{a(t)l} + P_{dia} + H_{ss(t)} \quad \text{Eqn. 36}$$

The geometric factor and non-geometric factor of a normalized supra-systolic cuff wave may be defined as follows: For the systolic cycle:

$$G_{ss(t)} = 1 \quad H_{ss(t)} = 0 \quad \text{Eqn. 37}$$

and for the diastolic cycle:

$$G_{ss(t)} = 1 \quad H_{ss(t)} = F_{(t)} \quad \text{Eqn. 38}$$

where, $F_{(t)}$ is an oscillation function of higher order harmonics.

Figure 8A:
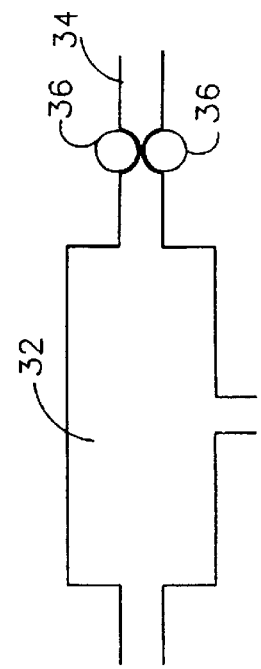
FIG. 8A is a graphical representation of an arterial pressure wave at a supra-systolic pressure.
Figure 8:
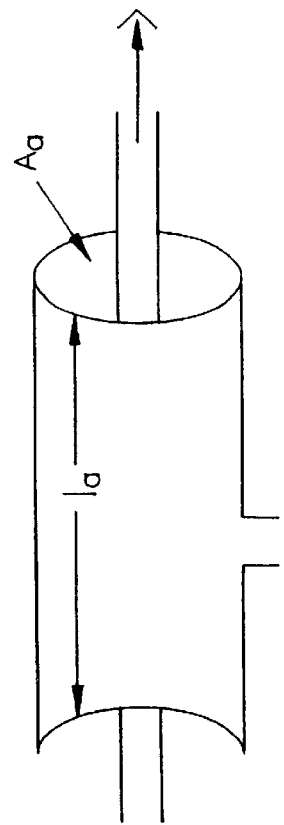
FIG. 8 is a schematic representation of an arterial system at a supra-systolic condition.
Figure 9:
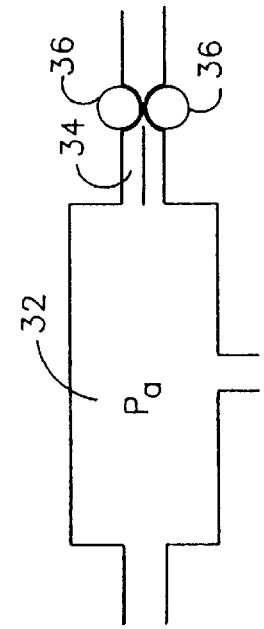
FIG. 9 is a schematic representation of an arterial system at a sub-diastolic pressure.

Turning now to FIG. 8A, the pressure wave can be represented graphically as follows. When the blood pressure cuff is exerting less pressure on the arm than the patient's diastolic pressure (a sub-diastolic pressure), the patient's cardiovascular system, and in particular his aorta/artery system behaves differently than it behaves when the cuff is exerting a supra-systolic pressure. Turning now to FIG. 9, a cardiovascular system wherein the cuff is exerting a sub-diastolic pressure is illustrated. You will notice that the brachial artery 34 is unobstructed by the cuff 36. Because the blood flows through the brachial artery 34 unobstructed by the cuff 36, the sub-diastolic cuff pressure wave ($P_{sd(t)}$) may be obtained, in a manner similar to the supra-systolic wave through the following equation:

$$P_{sd(t)} = [G_{sd(t)}P_{a(t)l}] + P_{dia} + H_{sd(t)} \quad \text{Eqn. 39}$$

where, $G_{sd(t)}$ and $H_{sd(t)}$ are the respective geometric factor and non-geometric factor of the artery/aorta system of the patient.

The geometric factor and non-geometric factor of a sub-diastolic wave may be defined as follows:

$$G_{sd(t)} = 1 \quad H_{sd(t)} = 0 \quad \text{Eqn. 40}$$

for the systolic cycle; and $$G_{sd(t)} = 1 \quad H_{sd(t)} > 0 \quad \text{Eqn. 41}$$

for the diastolic cycle

In order to obtain a pressure wave from a non-invasive cuff system that is similar to the pressure wave obtained from an invasive sensor system, it is important that the non-invasive sensors should be sensitive to the same frequency range as the frequency range to which the invasive catheter device sensors are sensitive. If one assumes that a high frequency sensor and a low frequency sensor are used, a non-invasive cuff pulse wave ($P_{n(t)}$), may be redefined as $$P_{n(t)} = G_{n(t)}[P_{a(t)1h} + P_{a(t)1l}] + P_{dia} + H_{n(t)} \quad \text{Eqn. 42}$$

where "h" and "l" indicate the high and low frequency components, respectively, and "n" indicates the non-invasive cuff measurement of the pulse wave.

When a blood pressure cuff is inflated to a higher pressure, it generally tends to be more sensitive to higher frequency pulses. Conversely, when a cuff is inflated to a lower cuff pressure, it tends to be more sensitive to lower frequency signals. Therefore, the supra-systolic and sub-diastolic waves, Eqns. 36 and 39, may be redefined as follows:

$$P_{ss(t)} = G_{ss(t)}[P_{a(t)1H} + P_{dia} + H_{ss(t)}] \quad \text{Eqn. 43}$$

$$P_{sd(t)} = G_{sd(t)}[P_{a(t)1L} + P_{dia} + H_{sd(t)}] \quad \text{Eqn. 44}$$

Additionally, when one incorporates the assumptions discussed above for the geometric factors (G) and the non-geometric factors (H) as discussed above, from Eqns. 43 and 44, one may reconstruct a pseudo-catheter (aorta/artery) invasive waveform ($P_{(t)}$) from the non-invasive supra-systolic and sub-diastolic cuff waveforms. In this regard, it is generally preferred for reasons of clarity to discuss the formation of a pseudo-invasive arterial wave ($P_{(t)}$) by considering the systolic curve, the systolic wave (SW), and the diastolic cycle and diastolic wave (DW) separately from each other. In this application, the term "pseudo" when placed in front of a term designating a waveform (e.g.

pseudo aortic wave, pseudo aortic wave contour, pseudo invasive arterial wave, etc.) is used to designate a waveform which is not measured directly but rather is created from the manipulation of data to construct a model that approximates the waveform of interest.

C. The Systolic Wave

Since $G_{ss}$ equals 0, $G_{sd}=1$, $H_{ss}=0$, and $H_{sd}$ is very small, and may therefore be neglected, Equations 43 and 44 can be transformed as follows:

$$P_{ss(t)}=P_{a(t)1H}+P_{dia}=P_{a(t)H} \quad \text{Eqn. 46}$$

$$P_{sd(t)}=P_{a(t)1L}+P_{dia}=P_{a(t)L} \quad \text{Eqn. 47}$$

where $P_{a(t)H}$ and $P_{a(t)L}$ are the high and low frequency components of the aortic pressure at a particular time ($P_{a(t)}$), the pressure of a pseudo-invasive systolic wave ($P_{sw(t)}$), may be obtained by assuming certain weights on the supra-systolic and sub-diastolic waves. Assuming these certain weights leads to the following equation that describes the pressure of the systolic wave at a particular time.

$$P_{sw(t)} = \frac{[W_{ss}][P_{ss(t)}] + [W_{sd}][P_{sd(t)}]}{W_{ss} + W_{sd}} \quad \text{Eqn. 48}$$

where $W_{ss}$ is the weight assigned to the supra-systolic wave component, and $W_{sd}$ is the weight assigned to the sub-diastolic wave component. The weights that are assigned to the respective supra-systolic and sub-diastolic wave components ($W_{ss}$ and $W_{sd}$) can be determined empirically. In order to determine these empirically, one does the following:

First, one selects the values for the weight to be assigned to the respective supra-systolic and sub-diastolic wave components ($W_{ss}$ and $W_{sd}$), and uses these values to construct the pseudo-invasive systolic wave ($P_{sw}(t)$), according to Equation 48. Next, one compares the determined pseudo-invasive systolic wave to an invasive catheterization, aortic pressure wave ($P_a(t)$).

One then tries to find the best fit of the pseudo-invasive systolic wave ($P_{sw}(t)$) to the invasive catheterization aortic pressure wave ($P_a(t)$) and use these to determine the weights that are assigned to the respective supra-systolic and sub-diastolic wave components ($W_{ss}$ and $W_{sd}$).

Figure 7:
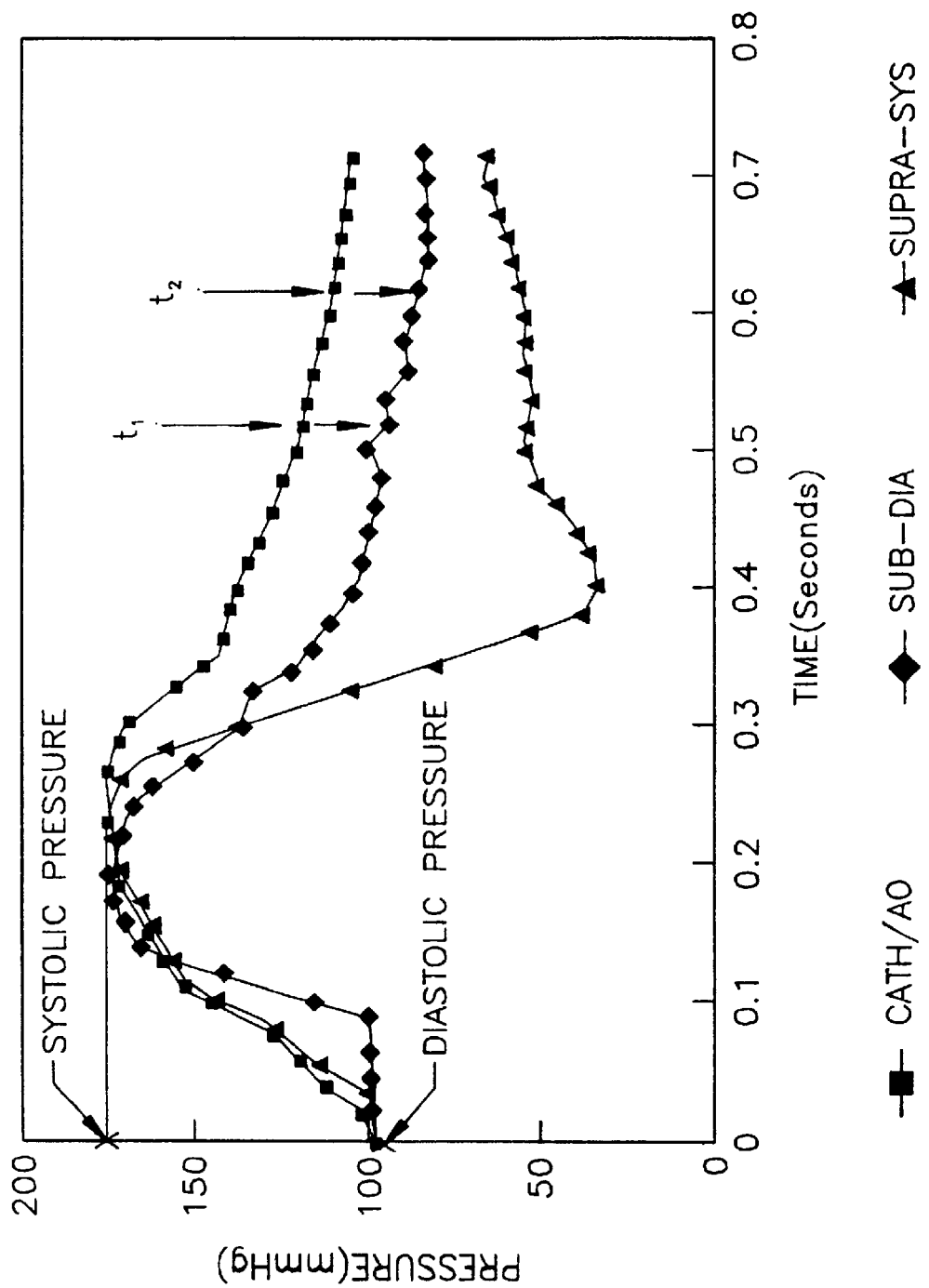
FIG. 7 is a graphical representation of an aortic pulse pressure wave taken through catheterization, and a supra-systolic and sub-diastolic pulse pressure wave form taken through the non-invasive method of the present invention.
Figure 12B:
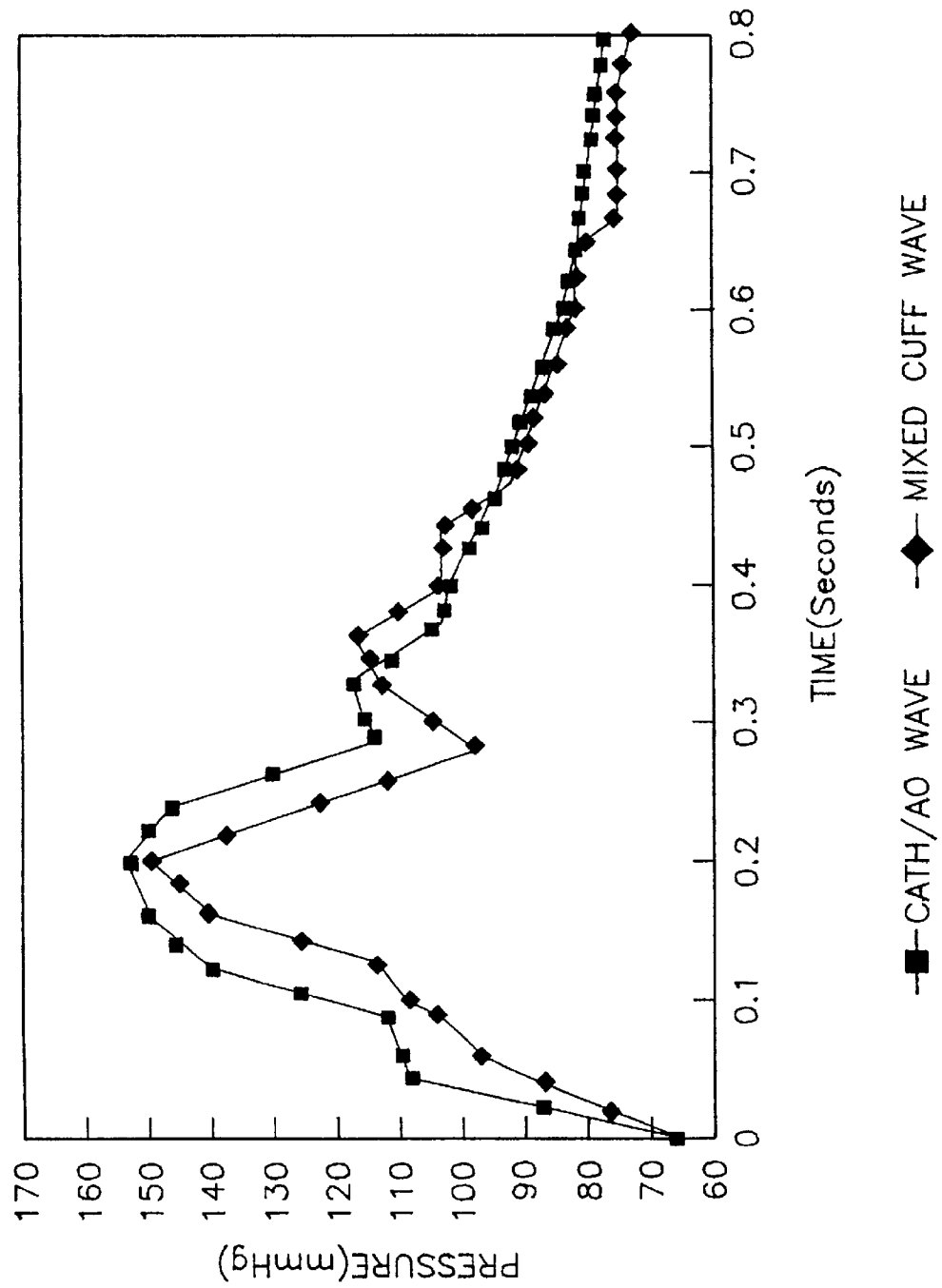
FIG. 12B is a graphical representation of a pseudo-aortic cuff wave determined from a non-invasive measurement according to the Applicant's invention which is plotted against an actual aortic wave taken from an invasive catheterization, illustrating an aortic sclerosis pathology cardiovascular condition.

The best fit wave factors of 17 patients are shown in Table 1, and an example of the fit is shown in FIGS. 7, 12A and 12B.

Through the testing conducted on the 17 subjects reported above in FIG. 1, the applicants found that the best fit yields the following mean weight factors:

$$W_{ss}=1, \; W_{sd}=0.4, \text{ and } W_d=0.6 \quad \text{Eqn. 48A}$$

The weight factors listed above represent "mean weight factors," and as such are generally applicable to most patients. As shown in Table 1, these weight factors have a standard deviation of 0, 0.29, and 0.19, respectively, which are the error values of the weight factors.

TABLE 1

WEIGHT FACTORS FOR THE BEST FIT OF NON-INVASIVE CUFF WAVES TO CATHETERIZATION AORTIC PRESSURE WAVE

| Subject | $W_{ss}$ | $W_{sd}$ | $W_d$ |
|---|---|---|---|
| 1 | 1 | 0.1 | 0.1 |
| 2 | 1 | 0.7 | 0.5 |
| 3 | 1 | 0.1 | 0.6 |
| 4 | 1 | 0.1 | 0.6 |
| 5 | 1 | 0.1 | 0.5 |
| 6 | 1 | 0.9 | 0.55 |
| 7 | 1 | 0.5 | 0.7 |
| 8 | 1 | 0.6 | 0.8 |
| 9 | 1 | 0.5 | 0.8 |
| 10 | 1 | 0.1 | 0.6 |
| 11 | 1 | 0.8 | 0.85 |
| 12 | 1 | 0.55 | 0.6 |
| 13 | 1 | 0.5 | 0.3 |
| 14 | 1 | 0.8 | 0.4 |
| 15 | 1 | 0.5 | 0.7 |
| 16 | 1 | 0.1 | 0.6 |
| 17 | 1 | 0.1 | 0.3 |
| mean | 1.00 | 0.41 | 0.56 |
| std. deviation | 0.00 | 0.29 | 0.19 |
| | weight factors used for creating pseudo-systolic wave, Eqn. 48 | | weight factors used for creating pseudo-dyastolic wave Eqn. 52 |

D. The Diastolic Wave

For the diastolic wave (DW), since $G_{ss}=0$, $G_d=1$, and since $H_{ss(t)}$ and $H_{sd(t)}$ are not equal to 0, Eqns. 43 and 44 can be transformed as follows to describe the diastolic wave.

$$P_{ss(t)}=P_{dia}+H_{ss(t)} \quad \text{Eqn. 50}$$

$$P_{sd(t)}=G_{sd(t)}P_{a(t)(1)(L)}+P_{dia}+H_{sd(t)}=P_{a(t)(L)}+H_{sd(t)} \quad \text{Eqn. 51}$$

During the diastolic cycle, the aorta-arterial system is at a lower blood pressure, and the cardiovascular system is generally in a state of relaxation. Therefore, the low frequency wave component dominates over the high frequency wave component. As such, $P_{at}=P_{a(t)}L$. Further, if one assumes that $H_{sd(t)}=(W_d)$ ($H_{ss(t)}$), a pseudo-invasive Diastolic Wave pressure ($P_{dw(t)}$), which equals the aortic pressure $P_{a(t)}$ may be derived as follows. In the following equation, "$W_d$" is a weight factor.

$$P_{dw(t)}=P_{sd(t)}+(W_d)(P_{dia}-P_{ss(t)}) \quad \text{Eqn. 52}$$

$W_d$ is a number which can be determined empirically, as discussed above in connection with Table 1, and Eqns. 48 and 48A.

III. Left Ventricular Pressure Wave and Aortic or Pseudo Aortic Pressure Waves

In the section above, the reconstruction of an aortic wave was set forth and discussed. Actually, a pseudo-aortic wave from an observation and mathematical manipulation of values was determined for cuff arterial waves. In an ideal case, since the systolic cycle of the aortic wave (the Systolic Wave (SW) as defined above) is a part of the left ventricular wave, their relation can be described by the graphical representation set forth in FIG. 11.

If one assumes simple Gaussian curves for both the aortic systolic wave, and the left ventricular systolic wave at a time "0" (which is the time of maximum pressure or the systolic point), the equations for the aortic systolic wave SW may be defined as follows:

$$P_{ao(t)} = P_p e^{\frac{-t^2}{2(Ta)^2}} + p_{dia} \quad \text{Eqn. 53}$$

In Eqn. 53, $P_p$=the pulse pressure; $T_a=\frac{1}{2} T_{pp}$ of the aortic wave and $P_{dia}$=the diastolic pressure.

Similarly, the equation for the pressure of the left ventricular (LV) systolic wave ($P_{LV(t)}$) can be defined as follows:

$$P_{Lv(t)} = P_{sys} e^{\frac{-t^2}{2(Tv)^2}} \quad \text{Eqn. 54}$$

where $P_{sys}$=the systolic pressure and $T_v=\frac{1}{2} T_{pp}$ of the LV (left ventricular) wave; where $T_{pp}$=the time between the maximum change of pressure over time, and minimum pressure over time of the left ventricular wave. In this regard, it should be noted that $T_{pp}$ of the aortic systolic wave is generally less than the $T_{pp}$ of the left ventricular wave.

From the above equations, the maximum, $$\left[\left(\frac{dP}{dt}\right)LV\right]_{max} \quad \text{Eqn. 55}$$

or, since the Gaussian curve is symmetrical, the minimum $$\left[\left(\frac{dP}{dt}\right)LV\right]_{min} = -\left[\left(\frac{dP}{dt}\right)LV\right]_{max} \quad \text{Eqn. 55A}$$

left ventricular contractility can be derived as follows:

$$\left[\left(\frac{dP}{dt}\right)LV\right]_{max} = \left[\frac{\left(\frac{dP}{dt}\right)_{max} aorta}{T_r}\right] e^{\frac{1}{2}(Tr^2-1)} \quad \text{Eqn. 56}$$

In Equation 55, $$T_r = \frac{T_a}{t_v} = \left[1 + \left[\frac{P_{pia}}{P_p}\right]\left[e^{\frac{1}{2}}\right]\right]^{-\frac{1}{2}} \quad \text{Eqn. 57}$$

Other cardiac parameters may also be able to be obtained using the above model.

Where $T_r = \frac{T_a}{t_v}$; $T_a = \frac{1}{2}[T_{pp}]_{aorta}$; and $T_v = \frac{1}{2}[T_{pp}]_{LV}$

IV. Operation of the Present Invention

A. Gathering Cardiovascular Condition Information

The first step in either determining a particular hemodynamic parameter (e.g. peripheral resistance, cardiac output, blood pressure, etc.), or diagnosing a cardiovascular pathology (e.g. hypertension, etc.), is to gather information about the patient's cardiovascular condition. The preferred method for gathering this information is that method taught in Chio's U.S. Pat. No. 4,880,013.

The Chio method and apparatus relate to a non-invasive means and device for gatherings information about the cardiovascular condition of a patient. Chio's method consists of using an inflatable cuff and a means for picking up the pressure wave signals made by a cardiovascular system during the use of the cuff. The cardiovascular noises are transmitted by a transducer, which converts the pressure wave signals from audio signals into electrical signals. The analog-type electrical signals so obtained are converted by an analog-to-digital converter, and fed to a processing unit, such as a software containing personal computer for processing the information received. The data stream of information is processed by the computer into a usable graphic display. The "base" displays of the data stream is a graphical representation wherein pulsation signal data is displayed as a function of either cuff pressure, or time.

The computer can include software for manipulating the data stream to display other characteristics of the data stream. The display of pulse pressure as a function of time (and cuff pressure) will appear similar to the information shown in FIG. 2 of the Chio '013 patent. As the Chio method is described in greater detail in the Chio '013 patent, it will not be repeated here, but rather incorporated by reference into the instant patent application.

The Chio method bears a similarity to most known methods for obtaining blood pressure, in that the blood pressure cuff is first elevated to a pressure above the patient's expected systolic blood pressure. This "supra-systolic" blood pressure comprises the starting point for the acquisition of data. Over time, the cuff pressure is decreased, past the systolic pressure, into the range of pressure between the systolic and diastolic pressures, and then finally terminates at a point below the patient's determined diastolic pressure. As will be discussed in more detail below, the pulse waveforms that are obtained in the supra-systolic and sub-diastolic regions have been found by the Applicant to be especially useful in determining some of the hemodynamic parameters of interest of the present invention.

From this data stream (and the waveforms so created), the patient's systolic blood pressure, diastolic blood pressure, and mean arterial pressure can be determined.

If one desires to use the Chio method, one can do so by purchase of the DYNAPULSE Blood Pressure Monitor Device manufactured by Pulse-Metric, Inc., the assignee of the present invention. As discussed above, a data stream of information should be obtained which includes both supra-systolic and sub-diastolic information, along with information in the area between the systolic pressure and the diastolic pressure.

Figure 13:
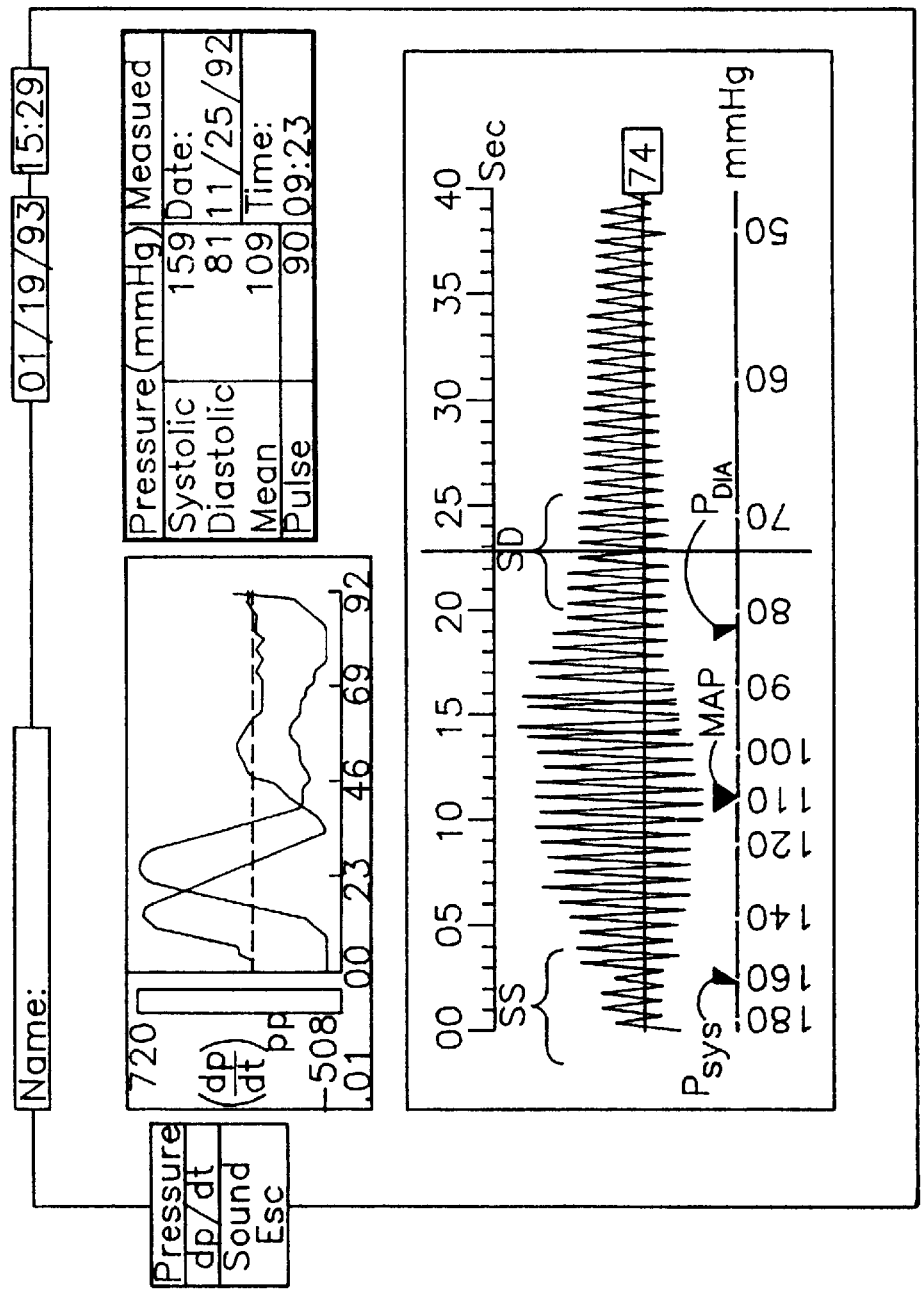
FIG. 13 is a sample output taken from a DYNAPLULSE blood pressure device showing a typical series of cardiovascular wave forms.

Turning now to FIG. 13, a sample output is shown from the DYNAPULSE Blood Pressure Monitor Device. Those waveforms, and that information in the range of between about 180 and 160 mmHg represents the supra-systolic information obtained from the device. In FIG. 22, the systolic pressure was determined to be 159 mmHg. The information between the determined systolic pressure (159 mmHg) and the determine diastolic pressure (81 mmHg) represents that information in the area between the determined systolic pressure and the determined diastolic pressure. As expected, the mean arterial pressure (109 mmHg), occurs in this range. The material received between 81 mmHg and the end of the test (approximately 45 mmHg) comprises the sub-diastolic information. Of this sub-diastolic information, the information of particular interest is that information at the near-sub-diastolic range between about 81 mmHg and about 65 mmHg.

In addition to the transducer disclosed in the Chio '013 patent, and used in connection with the DYNAPULSE Blood Pressure Monitor, one may also use other pressure sensing devices, such as an ultrasound probe which are placed in the area of the artery upstream from the position of the pressure inducing cuff.

B. Determining Peripheral Resistance, and Diagnosing a Patient Using the Peripheral Resistance So Determined As discussed above, one first determines the systolic, diastolic and mean arterial pressures from the data stream of information so taken. Along with other uses (described below) one use of the determined systolic and diastolic pressures is to define the supra-systolic and sub-diastolic regions. Pulse wave information taken from the supra-systolic region (supra-systolic pulse waves) is important because the arterial pulse waves measured at a supra-systolic pressure are measured at a pressure which exceeds the systolic point. The physiological importance of the supra-systolic segment of the pulse waves is that above the systolic point, no blood is flowing through the cuff area.

Similarly, the sub-diastolic waves are those arterial pulse waves which are measured at a cuff (or similar pressure sensing device) when the pressure inducing device (e.g. the cuff) is inducing a pressure on the artery which is less than the diastolic pressure. The sub-diastolic pulse waves can be obtained by a pressure inducing cuff device, or by other pressure sensing means, such as an ultrasound probe. The physiological significance of the diastolic pressure is that the pulse waves detected at sub-diastolic blood pressures represent a condition of unimpeded blood flow through the artery.

Once the supra-systolic and sub-diastolic waveforms are obtained, along with the systolic, diastolic and mean arterial pressures, the next step is to normalize the supra-systolic and sub-diastolic waves to systolic and diastolic points. In order to normalize these waves, one first assumes that the maximum point of both the supra-systolic and sub-diastolic waves occur at the systolic pressure. Further, one should assume that the beginning of the systolic cycle of the supra-systolic wave, and the lowest point of the sub-diastolic wave occur at the diastolic pressure. Through these assumptions, both the supra-systolic and sub-diastolic waves can be normalized to systolic and diastolic pressures as shown in FIG. 7. In FIG. 7, it will be noted that the normalized supra-systolic and sub-diastolic waves are plotted together with an aortic pressure wave that was obtained by an invasive, catheterization method. In the example shown in FIG. 7, the normalized non-invasive waves and the invasive catheterization waves have their systolic pressures at 171 mmHg, their diastolic pressures at 96 mmHg, and their mean arterial pressures at 116 mmHg. This "normalizing" procedure is based on Applicant's observations, and on an understanding of the theory underlying the aortic cycle. As described in Eqn. 46, the supra-systolic wave is dominated by the "harmonic" (non-geometric) component $P_{a(t)H}$. Therefore, a supra-systolic wave should appear similar to that shown in FIG. 8A, with its starting point or a "mean line" at the diastolic pressure, and its peak at systolic pressure. It has been found by Applicant that both invasive waves and non-invasive sub-diastolic waves have their peak at systolic, and their nadir points at diastolic.

The next step is to use Eqn. 31 to calculate the diastolic flow $V_o$ (which of course is related directly to the peripheral resistance and the pressure gradient). In order to use Eqn. 31, one must also determine the effective length of the blood pressure cuff ($l_{cuff}$) from which the data stream is obtained; the time between peaks of adjacent waveforms ($T_{pp}$); the change in pressure over time (or the slope) of a diastolic wave $$\left(\frac{dP}{dt}\right)_{DW} \qquad \text{Eqn. 33}$$

and the peak-to-peak change in the slope of a systolic wave $$\left(\frac{dP}{dt}\right)_{pp} \qquad \text{Eqn. 32}$$

With respect to the above-mentioned variables, the effective length of the blood pressure cuff ($l_{cuff}$) can be measured. The typical effective length of the standard adult size blood pressure cuff is typically about 9 cm.

The time between peaks of adjacent waveforms can be determined empirically, from the pulse waveforms of the data stream. For example, in the data stream shown in FIG. 12A, the change in pressure over time of the diastolic wave can be determined from the pseudo-aortic wave by obtaining the pressure difference between the pressure at time t, (0.5 seconds) and time $t_2$ (0.6 seconds). In this case, the pressure at time t, is 122 mmHg, the pressure at time $t_2$ is 111 mmHg, and the difference therebetween is 122−111=11 mmHg. Therefore, the change in pressure over time (dP/dt) equals, 11 mmHg/0.1 sec, or 110 mmHg/sec. Similarly, the maximum and minimum changes in pressure over time of the supra-systolic wave can be determined from the first derivative of the systolic wave with respect to time. Through the use of Eqn. 14, $(dP/dt)_{pp}$ can be obtained. Further, the time period between the maximum and minimum changes in pressure can be determined from the first derivative curve.

Figure 14:
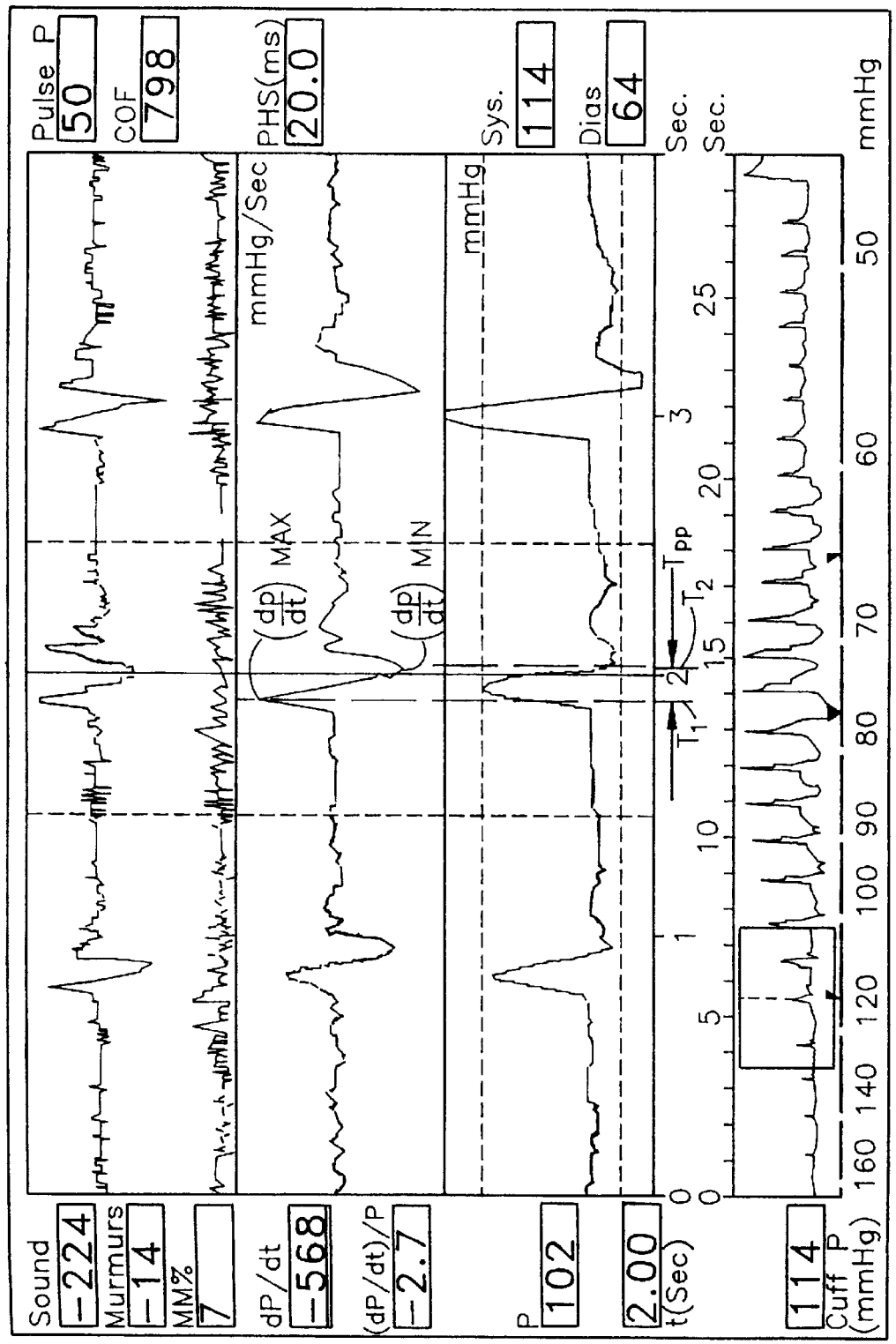
FIG. 14 is a sample output taken from a DYNAPULSE blood pressure device containing programming to display a first derivative curve (dP/dt) of a portion of the pulse pressure curve of a patient.

The first derivative curve can be obtained through proper programming of the central processing unit that is used in conjunction with obtaining and processing the patient's data stream of information. Turning now to FIG. 14, a display from a DYNAPULSE blood pressure monitoring device is shown. As the first derivative curve is a plot of the change in pressure over time (dP/dt), the maximum change in pressure over time $(dP/dt)_{max}$ and minimum change in pressure over time, $(dP/dt)_{min}$ are readily apparent from the curve. In a preferred embodiment, the central processing unit can be programmed to (1) provide numerical values for $(dP/dt)_{max}$ and $(dP/dt)_{min}$; (2) determine $T_{pp}$ from determined values of $t_1$ and $t_2$; and (3) solve Eqn. 14 from the determined values of $(dP/dt)_{max}$ and $(dP/dt)_{min}$.

One uses Equation 48 to determine the pressure of a systolic wave at a given time $T_{(sw)(t)}$ and to determine the change in pressure over time of the diastolic wave (dP/dt)$_{(dW)}$.

Once one determines the change in pressure over time of the diastolic wave and the maximum and minimum changes in pressure over time through the use of Eqn. 48, one can then determine the diastolic flow velocity ($V_o$) according to Eqn. 31 reprinted below $$V_o = \left[\frac{(4\pi)(l_{cuff})}{T_{pp}}\right]\left[\frac{\left(\frac{dP}{dt}\right)_{DW}}{\left(\frac{dP}{dt}\right)_{pp}}\right] \qquad \text{Eqn. 31}$$

From the knowledge of the diastolic flow velocity, one can then calculate either the distal peripheral resistance ($PR_2$), or the systemic peripheral resistance ($PR_1$) from diastolic flow velocity determined above, and the peripheral resistance parameter equations set forth at page 8, supra.

More particularly, the systemic peripheral resistance can be obtained via the following Eqn. 58.

$$PR_1 = \frac{\text{Systolic Pressure} - \text{Diastolic Pressure}}{V_0}$$

Similarly, one can determine the distal peripheral ($PR_2$) through Equation 59, which shows the results of the peripheral resistance that was measured and determined by the Applicant. In particular, FIG. 1 shows the determined distal peripheral resistance ($PR_2$) of 14 patients. This charting of determined peripheral resistance of the patients as a function of mean arterial pressure is useful in diagnosing the cardiovascular pathologies of the patients whose peripheral resistance was determined.

In order to diagnose the patient, one first determines a clinically significant threshold value, for serving as a line of demarcation between those who are likely to be at risk for having a particular cardiovascular pathology, and those who are not. In the instant case, the Applicant has used the known "bench mark" threshold values for systolic, diastolic and mean arterial pressures. The Applicant has also established a threshold value with respect to distal peripheral resistance also.

The standard threshold value for mean arterial pressure is 108 mmHg; for systolic pressure is 140 mmHg; and for diastolic is 90 mmHg. The threshold value determined by Applicant for peripheral resistance is 0.6 (mmHg) (sec/cm).

Using these threshold values, the Applicant believes that a patient can be diagnosed as having a reasonable possibility of having a high peripheral resistance type hypertension if (1) the mean arterial pressure is greater than 108 mmHg; or the systolic blood pressure is greater than 140 mmHg; or the diastolic blood pressure is greater than 90 mmHg; and (2) the distal peripheral resistance is greater than 0.6 (mmHg) (sec/cm).

It should be noted that the threshold value for distal peripheral resistance of 0.6 is a value that is likely to be modified, or better refined as further studies become available.

If a particular patient satisfies the criteria discussed above, he would generally be diagnosed as having a high peripheral resistance type hypertension. In such a case, the indicated treatment would appear to be the use of a vaso-dilator.

Additionally, the peripheral resistance can be used to diagnose those high cardiac output (CO) type hypertensive patients. The Applicant has found that these patients are those who typicallyhave a mean arterial pressure greater than 108 mmHg, or a systolic pressure greater than 140 mmHg, or a diastolic pressure greater than 90 mmHg. However, the high cardiac output-type hypertensive patients are distinguished from the high peripheral resistance type hypertensive patients in that the high cardiac output type hypertensive patients typically have a distal peripheral resistance of less than 0.6 (mmHg) (sec/cm).

Although the Applicant has performed experiments using distal peripheral resistance, it will also be appreciated that systemic peripheral resistance can also be used to determine hypertension, and to diagnose the difference between high peripheral resistance type hypertensive patients and high cardiac output type hypertensive patients.

Although the steps set forth above for determining peripheral resistance are described as being performed manually (to a large extent), it will be appreciated that a computer can be programmed to perform the processes described above for both determining peripheral resistance and diagnosing a patient based on the peripheral resistance and cardiac output so determined.

The peripheral resistance measurements discussed above can also be used to determine whether a patient has a high risk of having coronary artery disease. Once again, the peripheral resistance the mean arterial pressure that are determined from a patient are compared to threshold values. Based on the relation between the determined peripheral resistance and mean arterial pressure; and the threshold value, the patient can be diagnosed as either having a high, medium or low risk of having coronary artery disease. It has been found by the Applicant that generally patients have a high risk of having coronary artery disease if their mean arterial pressure is greater than 108 mmHg. Patients have a medium risk of having coronary artery disease if their mean arterial pressure is less than 108 mmHg, but their distal peripheral resistance is greater than the threshold value of 0.6 (mmHg) (sec/cm). Further, patients have a generally low risk of having coronary artery disease if both their mean arterial pressure and their distal peripheral resistance are lower than the threshold values of 108 mmHg, and 0.6 (mmHg) (sec/cm), respectively.

C. Determination of a Pseudo-Aortic Wave Contour, and Its Use for Determining Cardiovascular Pathologies Another aspect of the present invention is the determination of a pseudo-aortic pressure wave contour, and the use of this contour to help diagnose patients as having cardiovascular pathologies. In particular, the method is suitable for diagnosing cardiac aortic disease conditions.

In order to determine the pseudo-aortic pressure wave contour of a human cardiovascular system, a pressure inducing means and transducer is first affixed to a patient. A data stream is then obtained form the patient from the transducer means. The data stream includes pressure data and pulsation signal data. Preferably, the data stream includes data obtained at a supra-systolic pressure, at a sub-diastolic pressure, and at pressures in the range between the determined systolic pressure and diastolic pressure.

Using this pulsation signal data and pressure data, the pseudo-aortic pressure wave contour can then be determined.

In order to determine the pseudo-aortic pressure wave contour, one first uses the normalized supra-systolic wave and sub-diastolic wave data, as shown in FIG. 7, and as discussed above. An integration of Eqn. 48 is used to determine this data, including the weight factors for yielding the best fit that are disclosed in Eqn. 48a, and Table 1.

Once the pseudo-aortic pressure wave contour ($P_{sw(t)}$) is determined, one uses this normalized supra-systolic wave and sub-diastolic wave data in conjunction with Eqn. 52 to obtain the pseudo-diastolic wave contour $P_{dw(t)}$. Additionally, the weight ($W_{(d)}$ to be used in conjunction with Equation 52 is 0.6.

From this information, the pseudo-diastolic wave contour is obtained. The pseudo-systolic wave contour and the pseudo-diastolic wave contour are then combined to form the pseudo-aortic pressure wave as shown in FIGS. 12A and 12B. The reconstructed and normalized pseudo-aortic pressure wave contour carries a large amount of information about a patient's cardiovascular system. In principal, it can be used for diagnosing a large number of characteristics of a cardiovascular system, and a wide range of human hemodynamic parameters, and cardiovascular pathologies.

For example, the pseudo-aortic pressure wave contour can be compared to a chart of known cardiovascular pathologies. For example, the pseudo-aortic contour can be compared to the variations in contour of the arterial pulse with correlated ECGs, such as are shown at FIG. 4.2 of K. G. Andreoli, et al., Ed., *Comprehensive Cardiac Care,* C. V. Mosby Co., St. Louis, 1983.

A comparison of the contours can determine things such as arterial sclerosis. Turning now to FIG. 12B, the "notch" in the pseudo-aortic pressure wave that occurs between 101 and 115 mmHg, and 0.05 and 0.15 seconds is a notch that is very typical for patients having aortic sclerosis.

Turning now to FIG. 12A, a pseudo-aortic contour wave is shown that exhibits aortic stenosis. The stenosis in FIG. 12A is exhibited by the decrease in slope in the area designated 110 in the ascending portion of the systolic cycle of the pulse pressure wave. If one looks at the comparable portion of the pulse pressure wave of FIG. 12, it will be noted that the slope does not decrease as quickly in the patient not having stenosis.

D. Determining Cardiac Output and Diagnosing Cardiovascular Pathologies Relating to the Left Ventricle of the Heart In order to determine the peak left ventricular (cardiac) contractility of a human cardiovascular system, one first affixes a non-invasive pressure inducing means and transducer to a patient, to obtain a data stream from the transducer. The data stream should include pressure data and pulsation signal data. In these respects, the method for determining peak left ventricular (cardiac) contractility is generally similar to the methods discussed above. The method for obtaining the data stream disclosed in the Chio '013 patent is a preferred method for obtaining this data stream.

Once the data stream is obtained, the pulsation signal data and pressure data are used to determine the peak cardiac (LV) contractility by the following steps. First, the supra-systolic and sub-diastolic waves, along with Equation 48 (and the weight factors) are used to obtain a pseudo-systolic wave contour ($P_{sw(t)}$). The change in pressure over time of the diastolic wave is then determined, along with the peak-to-peak change in pressure over time.

Figure 11:
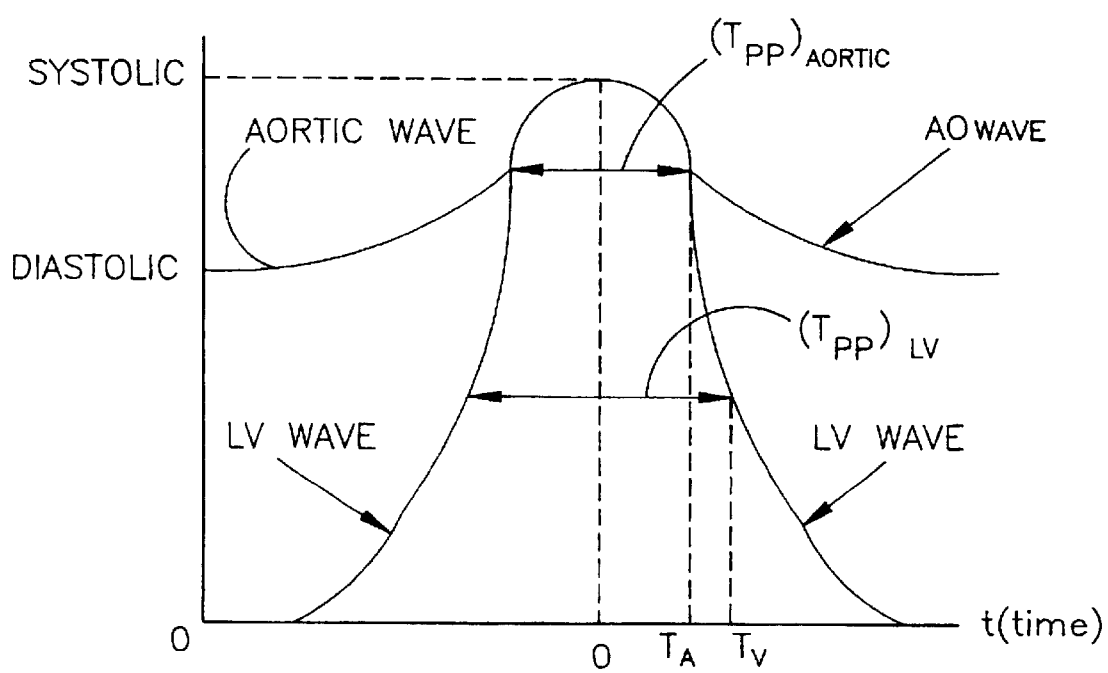
FIG. 11 is a graphical representation of the relation of the various temporal components of the aortic wave (AO), and the left ventricle (LV) wave.

Using Equation 57, and the measured systolic ($P_{sys}$) and diastolic ($P_{dia}$) pressures, and peak pressure ($P_p=P_{sys}-P_{dia}$), one can then calculate then Tr, which is the ratio of $T_{pp(aorta)}$ to $T_{pp(LV)}$ as defined above in Section III, (Equations 53–57) and FIG. 11. Using the above derived parameters and Eqn. 56, one can then calculate the peak cardiac contractility:

$$\left[\left(\frac{dP}{dt}\right)LV\right]_{max} \qquad \text{Eqn. 55}$$

The peak cardiac contractility may be used in the diagnosis of a cardiovascular pathology, as the peak cardiac contractility can be used as an index for determining the strength of the heart. As will be appreciated, the strength of the heart (or lack thereof) can be an important parameter for diagnosing a cardiac disease, or cardiac failure.

E. Determining Arterial Compliance and Elasticity of a Human Cardiovascular System The present invention can also be used for helping to determine arterial compliance ($C_o$) and elasticity ($K_e$) of a human cardiovascular system. In order to do this, one uses Eqns. 27 and 28. In so doing, one can either measure the arterial cross-section, or assume the arterial cross-section (for a normal) to be $A_o$ equals 0.67 cm2. One can further derive the arterial elastic constant Ke, and the compliance, which equals the inverse of the elasticity constant $\copyright$=1/Ke). Information about a person's arterial elasticity or a compliance is also a useful parameter for diagnosing the condition of the patient's cardiovascular system.

F. Use in Combination

Although the various factors and parameters have been discussed alone, it will be appreciated that the parameters so determined can be used in combination to diagnose a wide variety of disease, and to provide either supporting or contradictory evidence for other parameters so determined, and diagnoses so made.

G. Devices for Determining the Above Parameters

The methods discussed above can be incorporated into a device for automating the processes discussed above. The primary requirement of such a device is that it be capable of obtaining the information needed. One such device that is capable of obtaining the information is the DYNAPULSE 200M blood pressure monitor manufactured by Pulse-Metric, Inc. of San Diego, Calif., the assignee of the present invention. The DYNAPULSE device is described in more detail in the Chio '013 patent. It includes a blood pressure cuff for exerting a pressure on the art of a patient. A transducer is provided for capturing cardiovascular signals, and converting those cardiovascular signals into an electrical signal. An analog-to-digital converter is provided for converting the analoged noises to a digital information stream. The digital information stream is then processed by a CPU to create a variety of information displays. The relationships and equations discussed above in connection with the determination of the various parameters can be programmed into the CPU, to enable the device to provide a display or printout of a type that can be used by the practitioner attempting to determine the various parameters. Some of the parameters (e.g. peripheral resistance) may be best displayed digitally, as a numerical value. Others of the displays (e.g. the created pseudo-aortic wave) may be better displayed graphically. With regard to the pseudo-aortic contour, the device can also include a program for comparing an obtained pseudo-aortic wave to aortic waves of known cardiovascular pathologies, to suggest probabilities to a practitioner of a particular patient possessing a particular cardiovascular pathology (e.g. aortic sclerosis or stenosis). Alternately, the display might include a suggestion of alternatives diagnoses that the practitioner may wish to explore more fully through a visual diagnosis. In this regard, a wave form display has been found by Applicant to be a useful tool, itself, in determining the parameters discussed above, and for diagnosing cardiovascular pathologies.

V. WORKING EXAMPLES

The first step in obtaining the various parameters necessary for making the diagnoses of the instant application is to obtain a normalized supra-systolic and sub-diastolic pressure waves.

One first obtains the systolic, diastolic and mean arterial pressures of the patient. In the instant example, this was performed by the use of the DYNAPULSE Model 200M blood pressure device manufactured by Pulse-Metric, Inc., of San Diego, Calif., the assignee of the instant invention. The pressure wave so obtained from the patient is shown in FIG. 13.

As discussed earlier, the supra-systolic wave forms are wave forms taken at a pressure wherein no blood is flowing through the cuff area. Therefore, the arterial pulse waves measured at a cuff, or similar at a device at a supra-systolic pressure reflect this condition.

Turning now to FIG. 13, supra-systolic waves were obtained by using the DYNAPULSE device. A standard blood pressure cuff was used to occlude blood flow by applying a pressure to the artery greater than the systolic pressure. The supra-systolic waves were then obtained by using a transducer, and an analog-to-digital converter, as taught more explicitly in the Chio '013 patent. Alternately, one can use an ultra-sound probe to detect cardiovascular sound at a supra-systolic pressure.

As part of the procedure, the pressure exerted by the cuff was initially a pressure greater than the patient's systolic pressure. Over time, cuff pressure was reduced in a generally linear manner to a point below the patient's diastolic pressure. All during this time, pulse pressure waves were being obtained from the patient. Pulse pressure waves were obtained from the patient at pressures below the patient's determined diastolic pressure. The sub-diastolic pulse pressure waves were obtained at this sub-diastolic pressure. However, it will be appreciated that in situations where only certain information is needed (e.g. sub-diastolic and supra-systolic only) the device can be used to obtain only the information so required.

The supra-systolic (SS) and sub-diastolic (SD) waves were then normalized to the systolic ($P_{sys}$) and diastolic ($P_{dia}$) points. As discussed above, the systolic and diastolic pressures may be determined by use of the DYNAPULSE blood pressure monitor, or by any other method of determining blood pressure.

One then assumes that the maximum point of both the supra-systolic and sub-diastolic waves are the systolic pressure, and that the beginning of the systolic cycle of the supra-systolic wave, and the lowest point of the sub-diastolic waves are the diastolic pressures. Both the supra-systolic and sub-diastolic waves are then normalized to the systolic and diastolic pressures as shown in FIG. 7. Turning now to FIG. 7, the normalized supra-systolic and sub-diastolic waves are plotted together with an aortic pressure wave that was obtained by a catheterization method. In the example shown in FIG. 7, the normalized non-invasive waves and the invasive catheterization waves have their systolic pressure at 171 mm Hg, and their diastolic pressure at 96 mm Hg.

Once one obtains the normalized supra-systolic and the sub-diastolic pressures, one can use Equation 48 and Equation 52, with the appropriate wave factors ($W_{ss}$=1, $W_{sd}$=0.4, and $W_d$=0.6) to obtain the pseudo-aortic pressure waves, $P_{sw(t)}$ and $P_{dw(t)}$.

One then uses the normalized supra-systolic, sub-diastolic and pseudo-aortic waves to further calculate their slopes (dP/dt), at the maximum slope of the ascending portion of the pulse wave $(dP/dt)_{max}$, and at the maximum negative slope of the descending portion of the pulse wave $(dP/dt)_{min}$.

As discussed above in connection with the discussion of FIG. 12A, this process can be performed through appropriate programming of the central processing unit used in connection with the gathering of the information stream from the patient.

The peak values, $[(dP/dt)_{max}$, and $(dP/dt)_{min}]$ are then obtained. Using Eqn. 14, $(dP/dt)_{pp}$ can then be obtained from the determined $(dP/dt)_{max}$, and $(dP/dt)_{min}$.

In the example shown in FIG. 7, the variables necessary for using Equation 31 were determined as follows:

$L_{cuff}$ equals 9 cm, when using a standard adult size cuff having a width of 5 inches;

$T_{pp}$ equals 0.24 seconds, the time between the peak maximum change in pressure over time $(dP/dt)_{max}$, and the peak minimum change in pressure over time $(dP/dt)_{min}$;

$(dP/dt)_{pp}$ equals 1250 mm Hg/sec.; and $(dP/dt)_{DW}$ equals 62.5 mm Hg/sec.

Using these values, and Equation 31, the diastolic flow velocity for the patient whose cardiovascular information was obtained in FIG. 7 is $V_o$=23.56 cm/sec.

One then uses Equation 22 and assumes that the arterial cross-sectional area ($A_o$) equals 0.67 cm². From these values, one can further calculate the arterial compliance (C) as follows: C=0.26 cc/mm Hg.

One can then obtain the peripheral resistances ($PR_1$ and $PR_2$) using the following equations:

$$PR_1 = \frac{\text{Systolic Pressure} - \text{Diastolic Pressure}}{V_o} \qquad \text{Eqn. 58}$$

and $$PR_2 = \frac{\text{Mean Arterial Pressure} - \text{Diastolic Pressure}}{V_o} \qquad \text{Eqn. 59}$$

Using Equations 58 and 59, one can calculate both the proximal peripheral resistance ($PR_1$), and the distal peripheral resistance ($PR_2$). The values of the peripheral resistance for the patient whose cardiac information is shown in FIGS. 13 and 7 are:

$PR_1$=3.18 (mm Hg)(sec/cm); and $PR_2$=0.85 (mm Hg)(sec/cm).

Left ventricular (cardiac) peak contractility was then obtained by using pseudo-aortic systolic wave ($P_{sw(t)}$) and its peak change in pressure over time (dP/dt), along with Equations 56 and 57 to calculate the peak contractility of the left ventricle of the patient whose cardiac information is shown in FIG. 7.

$$\left[\left(\frac{dP}{dt}\right)LV\right]_{max} \qquad \text{Eqn. 55}$$

One example is illustrated. For a patient having a systolic pressure of 166 mm Hg, a determined diastolic pressure of 94 mm Hg, the pulse pressure ($P_p$) was calculated as 72 mm Hg, according to the numerator of Equation 58. Using Equation 57, one can calculate $T_r$, as being equal to 0.563.

The peak change in pressure over time was then obtained from the pseudo-aortic wave according to the following: $[(dP/dt)_{aorta}]_{max}$=804 mm Hg/sec. From this, one can calculate, using Equation 56, the peak left ventricular (cardiac) contractility. In the instant example, it was found that the peak cardiac contractility:

$$\left[\left(\frac{dP}{dt}\right)LV\right]_{max} \qquad \text{Eqn. 55}$$

equals 1015 mm Hg/sec.

The value so obtained by the applicant's non-invasive method was then compared to the value obtained from an invasive catheterization measurement. For the same patient, using the same information, the invasive catheterization measured a peak cardiac contractility of 1000 mm Hg/sec.

The general similarity of the results are used persuasively for the reliability of the Applicant's invention.

VI. Experimental Results

A. Hypertension Diagnosis

As part of the experimental procedure used to test the instant invention, the Applicant performed studies on various patients. Attached to this patent application, and submitted concurrently herewith, are several graphical representations showing information received during testing performed pursuant to this invention. These graphical plots include figures labeled FIGS. 2–6, and 8–11.

In order to test the theory of using the peripheral resistance ($PR_1$ and $PR_2$), defined above and derived from a measurement of the diastolic wave velocity, 14 human subjects, between the ages of 45 and 81 were studied. The invasive aortic pressure wave forms and non-invasive cuff pulse wave forms were obtained from these patients. Sub-diastolic wave forms were analyzed to obtain the parameters defined in Equation 31, supra. In these studies, the measured length of the cuff was 5 inches. This effective length was calculated by assuming that the effective length equaled the measured cuff length divided by the square root of 2. Thus, the effective length of the cuff having a measured length of 5 inches was equal to 3.5 inches. Further, it was found that the change in pressure over time of a diastolic wave (($dP/dt)_{DW}$) was calculated from the linear portion $T_1$ to $T_2$ of the diastolic wave (see, e.g., FIG. 11), and was confirmed by the invasive wave form. These values were then used in Equation 31.

Your attention is directed to FIG. 7, which illustrates the determination of the diastolic wave section, and its confirmation and comparison to the information derived from the invasive wave form.

Compliance was calculated through Equations 22 and 23 by assuming that a male subject having a height of 60 inches (5 feet) has an arterial cross-section of 1 cm$^2$, and that a female of the same height has an arterial cross-section of 0.8 cm$^2$. For different heights, the arterial cross-sections were adjusted accordingly by the following equation:

$$A_{o(x)} = (A_o)(\text{Height}_{(x)}/60).$$

FIGS. 2 through 6 of the Appendix, and FIG. 1 (of the instant application) display the results for both systemic peripheral resistance ($PR_1$) and distal peripheral resistance ($PR_2$), as both a function of the systolic, diastolic and mean arterial pressures of all 14 subjects. These results substantiate the Applicant's finding that either systemic peripheral resistance or distal peripheral resistance can be used for diagnosing hypertension. The Applicant also found that peripheral resistance is preferably plotted against either mean arterial or systolic pressure, since, for elderly people, their diastolic pressure may decrease, and the usual benchmarks for determining hypertensive systolic and diastolic pressures (140/90 mm Hg) may not be reliable indicators.

In FIGS. 8 and 9 of the Appendix are shown plots of the diastolic wave velocity plotted against systolic and diastolic readings taken from the 14 human subjects. The data suggests that people having a systolic blood pressure lower than 140 mm Hg, or diastolic blood pressure of less than 70 mm Hg tend to have lower diastolic wave velocity. However, for those patients having higher systolic and diastolic pressures, there appears to be one group of patients that has a higher diastolic wave velocity, whereas another group has a lower diastolic wave velocity. Since peripheral resistance equals mean arterial pressure divided by cardiac output, the group having a lower peripheral resistance may have a higher cardiac output. Therefore, the treatments of the two groups of high blood pressure should be different. This is discussed above.

FIGS. 10 and 11 of the Appendix are plots of the calculated compliances of the 14 subjects as a function of both systolic and diastolic pressures. Besides the scattering of the determined compliance values over a wide range of systolic and diastolic pressures, the Applicant has also noted that the trend of compliance compared to systolic pressure is opposite of the compliance when compared to diastolic pressure. This data suggests that compliance is not as valid and reliable of an indicator of hypertension as determined peripheral resistance determined in accordance with the present invention.

B. Reconstruction of Aortic Wave Forms

In the clinical data and from the discussions above, it was stated that it is possible to create an empirically fitted pseudo-aortic wave, using Equations 51 and 52. This pseudo-aortic wave may then be used for diagnosing certain cardiovascular pathologies, such as arterial stenosis, sclerosis, etc. Furthermore, it may provide further information on aortic valve and left ventricular characteristics. By using the data of the above 14 subjects, and appropriate wave factors, appropriate pseudo-aortic waves were able to be constructed. FIGS. 12A and 12B represent comparisons of pseudo-aortic waves constructed according to the present invention, and aortic waves measured by invasive catheterization.

C. Left Ventricular (Cardiac) Contractility From Cuff Pulse Wave Forms

Invasive catheterization left ventricular pressure waves and non-invasive cuff pulse wave forms of one human subject were recorded simultaneously. Using Equations 56 and 57, $P_{dia}$ and $F_p$ were determined using the non-invasive cuff. Additionally, $(dP/dt)_{max}$ was obtained from the use of a 90% supra-systolic and 10% sub-diastolic wave forms. Using this, an averaged:

$$\left[\left(\frac{dP}{dt}\right)LV\right]_{max} \qquad \text{Eqn. 55}$$

was calculated to be 968 (±139) mm Hg/sec. This compared favorably to the cardiac contractility of 1057 mm Hg/sec calculated from the invasive catheter derived left ventricular pressure wave. Since the systolic wave of the pseudo-aortic wave is not symmetric, the change in pressure over time of the ascending part of the wave equals approximately 675 mm Hg/sec, whereas the change in pressure over time of the descending portion of the wave approximates 900 mm Hg/sec. If one uses the value 900 as the maximum change of pressure over time for the aorta $(dP/dt)_{max}$, the left ventricular cardiac contractility calculated therefrom:

$$\left[\left(\frac{dP}{dt}\right)LV\right]_{max} \qquad \text{Eqn. 55}$$

becomes 1106 mm Hg/sec. Therefore, for an asymmetric aortic systolic wave, the Applicant believes that it is better to use the larger value of its change in pressure over time by calculating the cardiac/left ventricular contractility. This has some intuitive support since the slope of the ascending aortic wave may be decreased by aortic stenosis or sclerosis or other unknown factors.

Although the invention has been described in detail with reference to the illustrated preferred embodiments, variations and modifications exist within the scope and spirit of the invention as described and as defined in the following claims.

What is claimed is:

1. A method for diagnosing a patient as being at risk for having a cardiovascular pathology, comprising the steps of:
   a. affixing a non-invasive pressure inducing member and transducer member to the patient,
   b. elevating the pressure induced by the pressure inducing member to a supra-systolic pressure,
   c. decreasing the pressure induced by the pressure inducing member over time to a sub-diastolic pressure,
   d. obtaining a data stream from the transducer member, the data stream including pressure data and pulsation signal data to obtain a series of pulsation signal data waveforms, the waveforms including at least pulsation signal data taken at a supra-systolic pressure and pulsation signal data taken at a sub-diastolic pressure, e. creating a pseudo-aortic wave contour from the obtained supra-systolic waveform data and the sub-diastolic waveform data, and f. diagnosing the patient as having a cardiovascular pathology by comparing the pseudo-aortic wave contour to cardiovascular contours exhibiting known cardiovascular pathologies.

2. The method of claim 1, wherein the step of creating a pseudo-aortic wave contour comprises the step of creating a pseudo-aortic wave contour through an integration of the equations $$P_{sw(t)} = \frac{[W_{ss}][P_{ss}] + [W_{sd}][P_{sd(t)}]}{W_{ss} + W_{sd}},$$

and $$P_{dw(t)} = P_{sd(t)} + (W_d)(P_{dia} - P_{ss(t)})$$

where $P_{sw(t)}$ = the pressure of a pseudo-aortic systolic wave, at a given time $(t)$ $W_{ss}$ = a coefficient comprising the weight assigned to the supra-systolic wave component $P_{ss(t)}$ = the pressure of the supra-systolic wave component at a given time, $(t)$ $W_{sd}$ = a coefficient comprising the weight assigned to the sub-diastolic wave component, $P_{sd(t)}$ = the pressure of the sub-diastolic wave component at a given time $(t)$ $P_{dw(t)}$ = the pressure of a pseudo-aortic diastolic wave at a given time, $(t)$;

$P_{dia}$ = the determined diastolic pressure, and $W_d$ = a weight factor.

3. The method of claim 2, wherein $W_{ss}$ equals about 1, and $W_{sd}$ equals about 0.4, and $W_d$ equals about 0.56.

4. A device for constructing a pseudo-arterial waveform for use in diagnosing a patient as being at risk for having a cardiovascular pathology, the device comprising:

a non-invasive pressure inducing member and a transducer member capable of being affixed to the patient; wherein the pressure induced by the pressure inducing member is elevated to a supra-systolic pressure and thereafter the pressure induced by the pressure inducing member is decreased over time to a sub-diastolic pressure;

a converter member which converts a signal from the transducer member to a data stream, wherein the data stream includes pressure data and pulsation signal data to obtain a series of pulsation signal data waveforms, the waveforms including at least pulsation signal data correlating to supra-systolic pressure and pulsation signal data correlating to sub-diastolic pressure, and a processing member for constructing a pseudo-arterial wave contour from the supra-systolic waveform data and the sub-diastolic waveform data through an integration of the equations:

$$P_{sw(t)} = \frac{[W_{ss}][P_{ss}] + [W_{sd}][P_{sd(t)}]}{W_{ss} + W_{sd}},$$

and $$P_{dw(t)} = P_{sd(t)} + (W_d)(P_{dia} - P_{ss(t)})$$

where $P_{sw(t)}$ = the pressure of a pseudo-aortic systolic wave, at a given time $(t)$ $W_{ss}$ = a coefficient comprising the weight assigned to the supra-systolic wave component $P_{ss(t)}$ = the pressure of the supra-systolic wave component at a given time, $(t)$ $W_{sd}$ = a coefficient comprising the weight assigned to the sub-diastolic wave component, $P_{sd(t)}$ = the pressure of the sub-diastolic wave component at a given time $(t)$ $P_{dw(t)}$ = the pressure of a pseudo-aortic diastolic wave at a given time, $(t)$;

$P_{dia}$ = the determined diastolic pressure, and $W_d$ = a weight factor.

5. The device of claim 4, wherein the processing member is further capable of constructing a pseudo-aortic wave contour.

6. A method for diagnosing a patient as being at risk for having a cardiovascular pathology, comprising the steps of:

a. affixing a non-invasive pressure inducing member and transducer member to the patient, b. elevating the pressure induced by the pressure inducing member to a supra-systolic pressure, c. decreasing the pressure induced by the pressure inducing member over time to a sub-diastolic pressure, d. obtaining a data stream from the transducer member, the data stream including pressure data and pulsation signal data to obtain a series of pulsation signal data waveforms, the waveforms including at least pulsation signal data taken at a supra-systolic pressure and pulsation signal data taken at a sub-diastolic pressure, e. creating a pseudo-catheter arterial invasive wave contour from the obtained supra-systolic waveform data and the sub-diastolic waveform data, and f. diagnosing the patient as having a cardiovascular pathology by comparing the pseudo-catheter arterial invasive wave contour to cardiovascular contours exhibiting known cardiovascular pathologies.

7. The method of claim 6, wherein the comparison of the pseudo-catheter arterial invasive wave contour to the cardiovascular contours is carried out with a processing member.

8. The method of claim 6, wherein the step of creating a pseudo-catheter arterial invasive wave contour from the obtained supra-systolic waveform data and the sub-diastolic waveform data is governed by a derived equation for the pressure of the systolic wave at a particular time and by a derived equation for the pressure of the diastolic wave at a particular time $$P_{sw(t)} = \frac{[W_{ss}][P_{ss}] + [W_{sd}][P_{sd(t)}]}{W_{ss} + W_{sd}},$$

and $$P_{dw(t)} = P_{sd(t)} + (W_d)(P_{dia} - P_{ss(t)})$$

where $P_{sw(t)}$ = the pressure of a pseudo-aortic systolic wave, at a given time ($t$)

$W_{ss}$ = a coefficient comprising the weight assigned to the supra-systolic wave component $P_{ss(t)}$ = the pressure of the supra-systolic wave component at a given time, ($t$)

-continued $W_{sd}$ = a coefficient comprising the weight assigned to the sub-diastolic wave component, $P_{sd(t)}$ = the pressure of the sub-diastolic wave component at a given time ($t$)

$P_{dw(t)}$ = the pressure of a pseudo-aortic diastolic wave at a given time, ($t$);

$P_{dia}$ = the determined diastolic pressure, and $W_d$ = a weight factor.

9. The method of claim 8, wherein the weight factor, $W_d$, the coefficient, $W_{sd}$, and the coefficient, $W_{ss}$, are empirically determined.

* * * * *